US011484569B2

(12) United States Patent
Dore et al.

(10) Patent No.: US 11,484,569 B2
(45) Date of Patent: Nov. 1, 2022

(54) POLYPEPTIDE FOR USE IN THE PROTECTION OF OXYGEN SENSITIVE GRAM-POSITIVE BACTERIA

(71) Applicants: INSTITUT NATIONAL DE LA SANTE ET DE LA RECHERCHE MEDICALE (INSERM), Paris (FR); ASSISTANCE PUBLIQUE—HOPITAUX DE PARIS, Paris (FR); INSTITUT NATIONAL DE LA RECHERCHE AGRONOMIQUE (INRA), Paris (FR); Université Paris-Sud, Orsay (FR)

(72) Inventors: Joël Dore, Jouy-en-Josas (FR); Jamila Faivre, Villejuif (FR); Nicolas Moniaux, Villejuif (FR); Christian Brechot, Paris (FR); Marion Darnaud, Lyons (FR)

(73) Assignees: INSTITUT NATIONAL DE LA SANTE ET DE LA RECHERCHE MEDICALE (INSERM), Paris (FR); ASSISTANCE PUBLIQUE—HOPITAUX DE PARIS, Paris (FR); INSTITUT NATIONAL DE LA RECHERCHE AGRONOMIQUE (INRA), Paris (FR); UNIVERSITÉ PARIS-SUD, Orsay (FR)

( * ) Notice: Subject to any disclaimer, the term of this patent is extended or adjusted under 35 U.S.C. 154(b) by 62 days.

(21) Appl. No.: 16/630,252

(22) PCT Filed: Jul. 13, 2018

(86) PCT No.: PCT/EP2018/069133
§ 371 (c)(1),
(2) Date: Jan. 10, 2020

(87) PCT Pub. No.: WO2019/012128
PCT Pub. Date: Jan. 17, 2019

(65) Prior Publication Data
US 2021/0093694 A1   Apr. 1, 2021

(30) Foreign Application Priority Data

Jul. 13, 2017   (EP) ..................... 17305925

(51) Int. Cl.
*A61K 38/17*   (2006.01)
*A23L 33/19*   (2016.01)

(52) U.S. Cl.
CPC .......... *A61K 38/1709* (2013.01); *A23L 33/19* (2016.08)

(58) Field of Classification Search
CPC ....... A23L 33/19; A23L 5/00; A61K 38/1709; A61K 9/0053
(Continued)

(56) References Cited

U.S. PATENT DOCUMENTS

| 2010/0172922 A1 | 7/2010 | Hooper et al. |
| 2015/0190465 A1 | 7/2015 | Faivre et al. |

FOREIGN PATENT DOCUMENTS

| AU | 2016259423 | 12/2016 |
| WO | WO-2015158241 | 10/2015 |

OTHER PUBLICATIONS

NCI, Definition of "Ex vivo", https://www.cancer.gov/publications/dictionaries/cancer-terms/def/ex-vivo, accessed on Dec. 15, 2021.*

(Continued)

*Primary Examiner* — Julie Ha
*Assistant Examiner* — Erinne R Dabkowski
(74) *Attorney, Agent, or Firm* — B. Aaron Schulman, Esq.; Stites & Harbison, PLLC

(57) ABSTRACT

The invention concerns a Reg3α polypeptide (also known as Hepatocarcinoma-Intestine-Pancreas/Pancreatitis Associated Protein (HIP/PAP)) for use in the protection of oxygen sensitive gram-positive bacteria, compositions comprising the polypeptide and their use. The inventors have shown that an increase in the concentration of the h Reg3α lectin into the gastrointestinal tract (GIT) lumen of hReg3α-transgenic mice induced significant changes in the composition of the gut microbiota, and dramatically improved host resistance to intestinal inflammation. hReg3α exerted a potent antioxidant activity on intestinal epithelial cells during colitis, and in particular the ROS scavenging activity, in particular, by promoting the survival of highly oxygen sensitive bacteria. Inventors also showed that h Reg3α-transgenic mice resist better to DSS-induced colitis after antibiotherapy. Thus, the invention concerns a Reg3α polypeptide for use in the protection of oxygen sensitive gram-positive bacteria, notably the Ruminococcaceae, such as *Faecalibacterium prausnitzii*, and/or the Lachnospiraceae, such as *Roseburia intestinalis*; pharmaceutical compositions comprising the polypeptide and their use; and the use of this polypeptide for promoting ex vivo growth of oxygen sensitive gram-positive bacteria. The Reg3α polypeptide may be used for preventing or treating microbiota-related disease and/or disorder, particularly selected from inflammatory bowel disease (IBD), colitis, gastrointestinal infections, irritable bowel syndrome and other gastrointestinal functional diseases, gastrointestinal tract cancer, metabolic syndrome and obesity, diabetes, liver diseases, allergic diseases, neurodegenerative diseases and psychological disorders.

5 Claims, 13 Drawing Sheets

Figure 1:
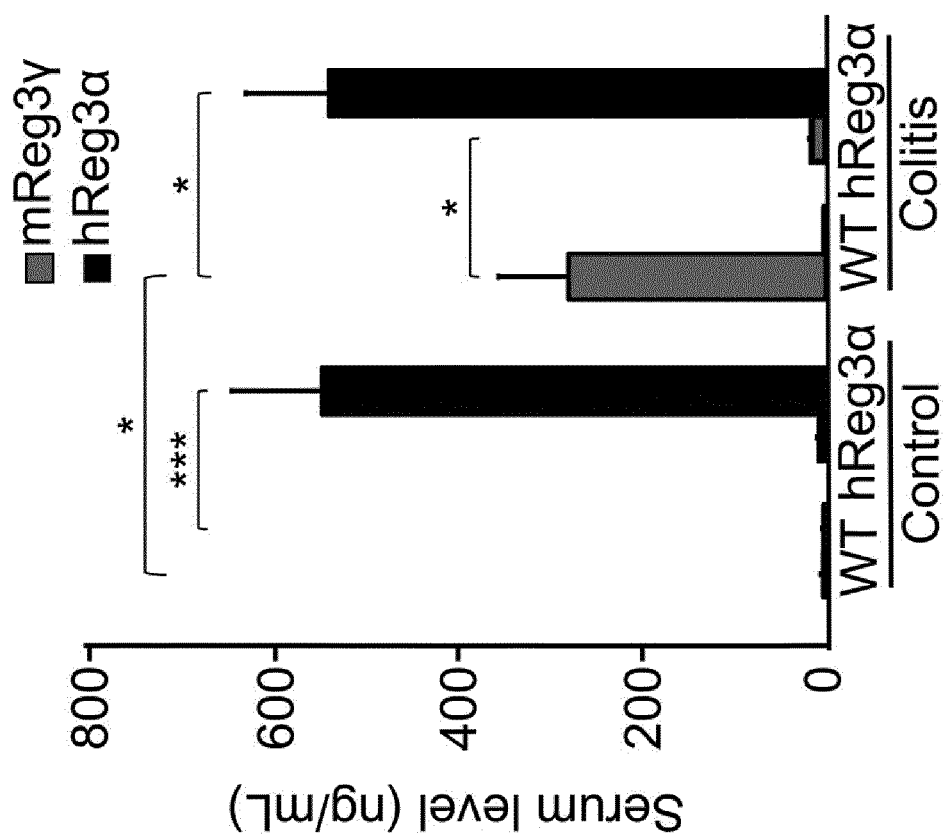

Specification includes a Sequence Listing.

(58) Field of Classification Search
USPC .......................................................... 514/2.4
See application file for complete search history.

(56) References Cited

OTHER PUBLICATIONS

Nicolas Moniaux et al: "HIP/PAP, un nouveau medicament contre les hepatites aigues graves", M/S Medecine Sciences., vol. 28, No. 3, Mar. 1, 2012 (Mar. 1, 2012), pp. 239-241, XP055432024, FR ISSN: 0767-0974, DOI: 10.1051/medsci/2012283004 the whole document.
Bertrand Nalpas et al: "A Proof of Concept, Phase II Randomized European Trial, on the Efficacy of ALF-5755, a Novel Extracellular Matrix-Targeted Antioxidant in Patients with Acute Liver Diseases", Plos One, vol. 11, No. 3, Mar. 16, 2016 (Mar. 16, 2016), p. e0150733, XP055432535, DOI: 10.1371/journal.pone.0150733 the whole document.
Omotayo Erejuwa et al: "Modulation of Gut Microbiota in the Management of Metabolic Disorders: The Prospects and Challenges", International Journal of Molecular Sciences, vol. 15, No. 3, Mar. 7, 2014 (Mar. 7, 2014), pp. 4158-4188, XP055432955, DOI: 10.3390/ijms15034158 the whole document.
International Search Report for PCT/EP2018/069133, dated Jul. 13, 2018.
Written Opinion for PCT/EP2018/069133, dated Jul. 13, 2018.
European Search Report for EP 17305925, dated Dec. 7, 2017.

\* cited by examiner

POLYPEPTIDE FOR USE IN THE PROTECTION OF OXYGEN SENSITIVE GRAM-POSITIVE BACTERIA

The present invention concerns a polypeptide for use in the protection of oxygen sensitive gram-positive bacteria, compositions comprising the polypeptide and their use, and the use of this polypeptide for promoting ex vivo growth of oxygen sensitive gram-positive bacteria.

TECHNICAL BACKGROUND

In mammals, and especially humans, the microbiota includes microorganisms such as bacteria, viruses, fungi and archaea (single-celled microorganisms) and can be found on skin including dermis and dermal adipose tissue, in the mouth, nose, respiratory tract, digestive tract and reproductive system. The microbiota has not only a commensal but also a mutualistic relationship with their host in that it preserves organ, tissue, and immune homeostasis locally and remotely. The microbiota performs several tasks among which trophic functions (epithelial cell turnover, gut motility, gut wall architecture, mucous membrane maturation, thickness, structure, etc.), metabolic functions (fat deposition, digestion, control of energy metabolism) and also defensive functions (antibacterial immunity, Paneth cell differentiation, barrier for exogenous bacteria or pathogens) and under normal circumstances they do not cause a disease or a disorder to the host. Under abnormal circumstance such as inflammation for example, there is an imbalance in the microbiota and said microbiota can influence host defence and immunity, and in turn may become pathogenic and contribute to disorder and/or disease initiation or exacerbations. This was especially observed with regards to the digestive tract microbiota.

Our gut microbiota contains tens of trillions of microorganisms, including at least 1000 different species of known bacteria with more than 3 million genes. Microbiota can, in total, weigh up to 2 kg. One third of our gut microbiota is common to most people, while two thirds are specific to each one of us. In mammals and especially in humans the gut microbiota is a community of microorganisms inhabiting the length and breadth of the gastrointestinal tract. The composition of this microbial community is host specific. Each individual's gut microbiota can undergo endogenous and exogenous alterations. It is also called human flora, microbiome, microflora or gut flora. In humans the gut microbiota is established at one to two years after birth, and by that time the intestinal epithelium and the intestinal mucosal barrier that it secretes have co-developed in a way that is tolerant to, and even supportive of, the gut microbiota and that also provides an efficient barrier to pathogenic organisms. The gut microbiota evolves from an immature and unstable ecosystem during infancy into a more complex and stable ecosystem in adulthood. Humans and gut microbiota are in a symbiotic relationship and the gut microbiota interacts with its host through bidirectional signalling connecting it to extra-intestinal organs (brain, liver) and influences its fitness and metabolism, which may contribute to metabolic diseases.

The gut microbiota plays a number of important roles including digestion, metabolism, extraction of nutrients, synthesis of vitamins, prevention against pathogen colonization, and modulation of the immune system.

In the gut microbiota of a healthy human, there is a balance between the beneficial bacteria and the potentially harmful or harmful ones. Health problems begin when there is an imbalance (due to antibiotic treatment as an example) of the gut microbiota.

If the quantity of harmful bacteria increases greatly, a variety of symptoms and pathologic states can arise. Such an imbalance is called dysbiosis or dysbacteriosis. It refers to an imbalance of microbial colonies, either in number or type, which have colonized the gut. This is most common in the digestive tract, but it can also happen in any exposed surface or mucous membrane of a human body where bacteria are present and active. Studies that aim to identify individual bacterial members of the microbiota that have the ability to promote immune maturation or inflammation repeatedly identify similar species or groups of organisms such as bacteria of the Prevotellaceae and adherent invasive *E. coli* (AIEC). These microorganisms have been named pathobionts to describe their potential pathogenic influence on the host. Although pathobionts coexist in the absence of overt disease in the healthy, immunocompetent host and significantly support maturation of the immune system, their influence might, under certain circumstances, drive inflammation, autoimmunity and promote the development of clinical diseases. Dysbiosis can affect digestion, absorption of nutrients, production of vitamins and controlling the growth of harmful microorganisms. A wide range of factors, such as changes in dietary habits or antibiotic use, can influence the delicate microbial balance and thus, lead to dysbiosis. Researchers believe that it may have a role in disorders such as Inflammatory Bowel Disease (IBD), chronic fatigue, obesity or certain cancers.

Alterations or changes in composition and/or biodiversity of the gut microbiota have been showed to be associated with microbiota-related diseases and disorders among which inflammatory bowel disease (IBD), gastrointestinal infections, irritable bowel syndrome and other gastrointestinal functional diseases, gastrointestinal tract cancer, non-gastrointestinal cancers (Pevsner-Fischer, Role of the microbiome in non-gastrointestinal cancers, World J Clin Oncol. 2016; 7(2): 200-213), metabolic syndrome and obesity, acute and chronic liver diseases, allergic diseases, autoimmune diseases (Kim D. Gut microbiota in autoimmunity: potential for clinical applications. Arch Pharm Res. 2016), cystic fibrosis (Nielsen S, Disrupted progression of the intestinal microbiota with age in children with cystic fibrosis. Sci Rep. 2016 May 4; 6:24857; Duytschaever G. Dysbiosis of bifidobacteria and *Clostridium* cluster XIVa in the cystic fibrosis fecal microbiota. J Cyst Fibros. 2013; 12(3): 206-15), atopic dermatitis and neurological diseases such as autism (Ianiro et al., Curr Drug Targets 2014; 15(8):762-70), anxiety, depression, and chronic pain (Mayer, Gut Microbes and the Brain: Paradigm Shift in Neuroscience. The Journal of Neuroscience, 2014, 34(46): 15490-15496).

Dysbiosis can be defined as an altered state of the microbiota occurring during diseases compared to the compositional and functional homeostasis in healthy individuals. Dysbiosis is currently viewed as a sign of an altered microbe-host crosstalk and is a primary target of strategies aiming at restoring or maintaining intestinal functional homeostasis. Although apparently restricted to microbiota composition and diversity, dysbiosis has been suspected to be a key pathogenic factor for a variety of gut and extra-gut diseases. Yet microbiota imbalance which comprises increased microbial biomass at the mucosal level, increased proportions of immuno-aggressive bacteria (essentially Gram negative) and, conversely, decreased proportions of immuno-protective bacteria (essentially Gram positive), triggers an auto-amplifying vicious circle.

The modulation of the gut microbiota in the management of the microbiota-related diseases and disorders is a promising approach for their treatment and/or prevention. Prior art relates to the use of probiotics, prebiotics, antimicrobial agents, bariatric surgery, and weight loss strategies (Omotayo et al., Int J Mol Sci. 2014 March; 15(3): 4158-4188).

The human secreted C-type lectin Reg3α, also known as Hepatocarcinoma-Intestine-Pancreas/Pancreatitis Associated Protein (HIP/PAP), is a 16 kDa carbohydrate-binding protein exhibiting anti-inflammatory activities in many eukaryotic cell types and tissues. It is expressed in Paneth's cells and the neuroendocrine cells of the small intestine under physiological conditions, and in the large intestine in response to infection and inflammation.

Truncated variant of Reg3α are known to be anti-inflammatory and/or antibacterial agents (U.S. Pat. Nos. 7,923,014 and 8,212,007).

The inventors have surprisingly discovered that contrary to the known antibacterial activity, Reg3α polypeptides permit to protect oxygen sensitive gram-positive bacteria. The present invention thus relies in the fact that the polypeptide Reg3α has a protective role for oxygen sensitive gram-positive bacteria and in particular for the beneficial symbionts of the gut microbiota.

SUMMARY OF THE INVENTION

The invention relates to a Reg3α polypeptide comprising the amino acid sequence SEQ ID NO: 4 or a sequence at least 85% identical thereto, for use in the protection of oxygen sensitive gram-positive bacteria.

Also provided is a pharmaceutical composition for oral or transmucosal administration comprising a Reg3α polypeptide which comprises the amino acid sequence SEQ ID NO: 4 or a sequence at least 85% identical thereto, in combination with at least one physiologically acceptable excipient.

The invention also relates to the use of the above defined composition for use for preventing or treating microbiota-related disease and/or disorder.

According to another aspect the invention relates to the use of a Reg3α polypeptide comprising the amino acid sequence SEQ ID NO: 4 or a sequence at least 85% identical thereto, for promoting ex vivo growth of oxygen sensitive gram-positive bacteria.

Also provided is the use of a Reg3α polypeptide comprising the amino acid sequence SEQ ID NO: 4 or a sequence at least 85% identical thereto, for the preparation of a food product.

DESCRIPTION OF THE INVENTION

The inventors have shown that an increase in the concentration of the hReg3α lectin into the gastrointestinal tract (GIT) lumen of transgenic mice induced significant changes in the composition of the gut microbiota, and dramatically improved host resistance to intestinal inflammation. In fact, hReg3α-transgenic mice exposed to DSS (dextran sodium sulphate) exhibited very few signs of colitis, retained a tight mucosal barrier and achieved complete survival. hReg3α exerted a potent antioxidant activity on intestinal epithelial cells during colitis, and in particular the ROS scavenging activity of a recombinant human Reg3α (rcReg3α) acted on prokaryote cells, in particular, by promoting the survival of highly oxygen sensitive bacteria.

The microbial changes exhibited by homozygous hReg3α-transgenic mice in homeostatic as well as inflammatory conditions mainly comprised an enrichment of Clostridiales (Ruminococcaceae, Lachnospiraceae) and a depletion of Bacteroidetes (Prevotellaceae). A systemic anticolitogenic effect was discarded since repeated intravenous administration of rcReg3α did not improve DSS-induced colitis in WT mice. Inventors showed that hReg3α provides protection against oxidative stress for both the intestinal epithelium and the commensal communities that form the gut microbiota. Inventors also showed that hReg3α-transgenic mice resist better to DSS-induced colitis after antibiotherapy.

The invention thus provides for a Reg3α polypeptide comprising the amino acid sequence SEQ ID NO: 4 or a sequence at least 85% identical thereto, for use in the protection of oxygen sensitive gram-positive bacteria.

Also provided is an in vivo or ex vivo method of protecting oxygen sensitive gram-positive bacteria comprising contacting oxygen sensitive gram-positive bacteria with a Reg3α polypeptide comprising the amino acid sequence SEQ ID NO: 4 or a sequence at least 85% identical thereto.

As used herein a "Reg3α polypeptide" denotes Regenerating islet-derived protein 3-alpha which is a pancreatic secretory protein having similarity to the C-type lectin superfamily. In an embodiment Reg3α polypeptide is a mammalian Reg3a, in particular, primate (preferably human) or rodent (such as rat or mouse) Reg3a. Reg3α may be native Reg3α or a naturally occurring or engineered variant thereof.

In the context of the invention the Reg3α polypeptide comprises the amino acid sequence SEQ ID NO: 4 or a sequence at least 85% identical thereto. The amino acid sequence SEQ ID NO: 4 is the sequence of trypsin truncated mature hReg3α. According to an embodiment, the Reg3α polypeptide comprises the amino acid sequence SEQ ID NO: 1 or a sequence at least 85% identical thereto. According to another embodiment, the Reg3α polypeptide comprises the amino acid sequence SEQ ID NO: 2 or a sequence at least 85% identical thereto. According to another embodiment, the Reg3α polypeptide comprises the amino acid sequence SEQ ID NO: 3 or a sequence at least 85% identical thereto.

The amino acid sequence SEQ ID NO: 1 is the sequence of hReg3α with its signal peptide (the signal peptide corresponding to amino acids 1-26). In vivo the hReg3α of sequence SEQ ID NO: 1 is processed to remove signal peptide and to form the mature hReg3α. Mature hReg3α has for sequence the amino acid sequence SEQ ID NO: 3.

Following a proteolytic cleavage by trypsin, an eleven amino acid stretch is removed from the N-terminus of mature protein Reg3a.

The amino acid sequence SEQ ID NO: 4 is the sequence of naturally occurring mature protein hReg3α, after trypsin cleavage; it corresponds to SEQ ID NO: 3 wherein the 11 first amino acids have been deleted.

The amino acid sequence SEQ ID NO: 2 is a sequence of hReg3α wherein the peptide signal sequence has been replaced by a Methionine. This sequence corresponds to recombinant mature protein.

Terms "a Reg3α polypeptide comprising the amino acid sequence of" as used herein refers to a polypeptide comprising an amino sequence having at least 85%, or at least 90%, 91%, 92%, 93%, 94%, 95%, 96%, 97%, 98%, or at least 99% identical to the amino acid sequence SEQ ID NO: 4. In some embodiment the polypeptide comprises an amino sequence having at least 85%, or at least 90%, 91%, 92%, 93%, 94%, 95%, 96%, 97%, 98%, or at least 99% of identity with the amino acid sequence SEQ ID NO: 1, SEQ ID NO: 2 or SEQ ID NO:3.

Amino acid sequence identity is defined as the percentage of amino acid residues in the sequence that are identical with the amino acid residues in the reference sequence, after aligning the sequences and introducing gaps, if necessary, to achieve the maximum percent sequence identity, and not considering any conservative substitutions as part of the sequence identity. Sequence identity may be determined over the full length of the analysed sequence, the full length of the reference sequence, or both. The percentage of identity for protein sequences may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5.

According to an embodiment, said Reg3α polypeptide protects oxygen sensitive gram-positive bacteria against one or more of the following conditions:

(i) intestinal inflammation;
(ii) exposure to oxygen, in particular to reactive oxygen species.

According to an embodiment, said Reg3α polypeptide allows the increase survival and growth of butyrate-producing bacteria, and of butyrate concentration which is an anti-inflammatory compound. Thus said Reg3α polypeptide permits the reduction of inflammation.

Terms "oxygen sensitive gram-positive bacteria" as used herein refers to gram-positive bacteria which are oxygen sensitive, as for example gram-positive members of the Clostridiales order, preferably gram-positive bacteria are of Ruminocaccaceae family and/or of Lachnospiraceae family, most preferably they are from *Faecalibacterium* genus and/or *Roseburia* genus, and more particularly they are *Faecalibacterium prausnitzii* and/or *Roseburia intestinalis*. In a preferred embodiment "oxygen sensitive gram-positive bacteria" are butyrate-producing bacteria. In a particular embodiment "oxygen sensitive gram-positive bacteria" are intestine bacteria known to produce butyrate.

Therapeutic Applications

According to another aspect of the invention, the Reg3α polypeptide as defined above is for use for preventing or a treating microbiota-related disease and/or disorder.

Also provided is a method of preventing or treating a microbiota-related disease and/or disorder comprising administering the Reg3α polypeptide as defined above to an host in need thereof.

As used herein, the term "preventing" refers to any method to partially or completely prevent or delay the onset of one or more symptoms or features of a microbiota-related disease and/or disorder. Prevention may be administered to a subject who does not exhibit signs of a microbiota-related disease and/or disorder.

As used herein, the term "treating" refers to any method used to partially or completely alleviate, relieve, inhibit, and/or reduce incidence of one or more symptoms or features and/or extending the lifespan of an individual suffering from a microbiota-related disease and/or disorder. In some embodiments, treatment may be administered to a subject who exhibits only early signs of the microbiota-related disease and/or disorder.

A subject as used herein relates to animals and preferably to mammals. More preferably the subject is a rodent and most preferably a mouse or a rate. In another embodiment of the invention the subject is a primate and most preferably a human. The subject can be suspected to suffer from a microbiota-related disease and/or disorder, or be at risk for developing microbiota-related disease and/or disorder.

As used herein, the terms "microbiota-related disease and/or disorder" refer to disease or disorder related to microbiota imbalance, and particularly to gut microbiota imbalance. "Microbiota-related disease and/or disorder" refer to disease or disorder selected from the group consisting of inflammatory bowel disease (IBD), colitis, gastrointestinal infections, irritable bowel syndrome and other gastrointestinal functional diseases, gastrointestinal tract cancer, metabolic syndrome and obesity, diabetes, liver diseases, allergic diseases, neurodegenerative diseases and psychological disorders. "Microbiota-related disease and/or disorder" may also refer to disease or disorder selected from the group consisting of autoimmune disease, cystic fibrosis, atopic dermatitis, neurological disease (such as autism), anxiety, depression, and chronic pain. In particular neurodegenerative diseases comprises Alzheimer disease and Parkinson. Microbiota-related disease and/or disorder may be due to lifestyle stressors that destroy gut microbiota balance such as medications of all types, antibiotics, chemotherapy, radiotherapy, immunotherapy, poor nutrition, eating disorders, illness, aging, and/or genetics.

The Reg3α polypeptide induces a depletion of bacteriodetes (Prevotellaceae), Sutterellaceae (phylum Proteobacteria) Porphyromonadaceae and Bacteroidaceae (phylum Bacteroidetes) in the gut microbiota.

In the context of the prevention or treatment of a microbiota-related disease and/or disorder, the Reg3α polypeptide may be administered through any suitable route of administration, such as oral, intravenous, rectal, sublingual, mucosal, nasal, ophthalmic, subcutaneous, intramuscular, transdermal, spinal, intrathecal, intra-articular, intra-arterial, sub-arachnoid, bronchial, or lymphatic administration. In a preferred embodiment, Reg3α is administered by oral or transmucosal route. In another preferred embodiment, Reg3α is administered by rectal route.

Preferably, the Reg3α polypeptide is provided in the form of a pharmaceutical composition which comprises the Reg3α polypeptide and at least one pharmaceutically acceptable excipient.

Pharmaceutical compositions used in the context of the invention are preferably designed to be appropriate for the selected route of administration, and pharmaceutically acceptable diluents, carriers, and/or excipients such as dispersing agents, buffers, surfactants, preservatives, solubilizing agents, isotonicity agents, stabilizing agents, and the like are used as appropriate.

As used herein, the term "pharmaceutically acceptable excipient" refers to any excipient suitable for use in contact with the tissues of the subject without excessive toxicity, irritation, allergic response, or other problem or complication, commensurate with a reasonable benefit/risk ratio.

In another aspect, the invention concerns a pharmaceutical composition for oral or transmucosal administration, or for use for oral or transmucosal, administration comprising the Reg3α polypeptide, in combination with at least one physiologically acceptable excipient. Said pharmaceutical composition is intended for oral or transmucosal administration and accordingly comprises at least one pharmaceutically acceptable excipient adapted for oral or transmucosal administration.

As used herein, the term "transmucosal administration" includes all types of administration through a mucosa and includes for example rectal, perlingual, pulmonary, vaginal or nasal administration. Preferably the type of administration can be adapted to the type of microbiota-related disease and/or disorder. In a preferred embodiment the composition according to the invention is for oral or rectal administration, more preferably the composition according to the invention is for rectal administration.

The pharmaceutical compositions according to the invention may be administered by transmucosal administration and be prepared, for example, as fast-dissolving tablets, emulsions, solutions, sprays, gels, mucoadhesive tablets or pastes, pastilles, sublingual tablets, drops, chewing tablets, suppositories or gums.

The pharmaceutical compositions according to the invention may be administered orally in the form of a suitable pharmaceutical unit dosage form. The pharmaceutical compositions of the invention may be prepared in many forms that include tablets, hard or soft gelatin capsules, aqueous solutions, suspensions, and liposomes and other slow-release formulations, such as shaped polymeric gels. The pharmaceutical compositions of the invention may be prepared in a gastro-protected form allowing the Reg3α polypeptide to pass the stomach and to be released in the intestine The pharmaceutical compositions according to the invention may be administered by rectal administration. The pharmaceutical compositions of the invention may be prepared in many forms that include compositions wherein the carrier is a solid for example as unit dose suppositories. Suitable carriers include cocoa butter and other materials commonly used in the art, and the suppositories may be conveniently formed by admixture of the pharmaceutical composition with the softened or melted carrier(s) followed by chilling and shaping in molds.

Each of these application forms can be produced by conventionally known formulation methods using formulation additives generally used for the production of such formulations. Such additives used for formulations described in the present invention may contain adjuvants or expedients etc. including solvents, buffers, flavoring agents, sweetening agents, fillers, preserving agents, gelling agents, carriers, diluents, surfactants and mucoadhesive polymers.

Preferred solvents which can be used according to the present invention are alcohols, especially ethanol, fatty acid esters, triglycerides, water and mixtures thereof.

Preferred preserving agents are lower alkyl parahydroxybenzoates, especially methyl and propyl parahydroxybenzoates.

Examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil.

As is well known in the medical arts, dosages for any one subject depend on many factors, including the patient's size, body surface area, age, the particular compound to be administered, sex, time and route of administration, general health, and other drugs being administered concurrently.

In another aspect the invention concerns the composition according to the invention for use for preventing or treating microbiota-related disease and/or disorder.

According to another aspect of the invention, the Reg3α polypeptide or the composition for oral or transmucosal administration according to the invention are for use for increasing the butyrate amount within the intestine.

Non Therapeutic Applications

All the definitions previously mentioned also apply to the said non therapeutic applications.

The present invention also concerns the use of a Reg3α polypeptide as defined above for promoting ex vivo growth of oxygen sensitive gram-positive bacteria.

Also provided is a method of promoting ex vivo viability and/or growth of oxygen sensitive gram-positive bacteria comprising contacting oxygen sensitive gram-positive bacteria with a Reg3α polypeptide as defined above.

Oxygen sensitive gram-positive bacteria are preferably bacteria of industrial interest such as Bifidobacteria genera, lactic acid-producing species or any of gram-positive probiotic bacteria. Probiotics are living microbial food additives that beneficially affect the host organism by improving its intestinal microbial balance. Beneficial effects of probiotics include reinforcing epithelial barrier, protecting against physiologic stress, and modulating gut associated lymphoid tissue. Most of the probiotic bacteria, in particular bifidobacteria, are sensitive microorganisms with low survival to stresses occurring during the production, storage and consumption of food products.

In an embodiment these bacteria are of particular interest in the formulation of food product and/or dietary supplement.

In an embodiment these bacteria are of particular interest for the production and/or the degradation of complex organic molecules such as complex carbohydrates and milk proteins.

As used herein, the term "ex vivo viability and/or growth" includes the viability and/or growth in fermenter and/or in product, such as food product (for example dairy product). Indeed it is difficult to obtain high yield of oxygen sensitive gram-positive bacteria because of the apparition of Reactive Oxygen Species (ROS). Use of a polypeptide according to the invention permits to protect oxygen sensitive gram-positive bacteria from oxidative stress and thus permits to obtain higher production yield.

As used herein, the term "promoting" includes the obtaining higher yields of oxygen sensitive gram-positive bacteria, or the possibility to use less strict anaerobic conditions for culturing of oxygen sensitive gram-positive bacteria while attaining similar yields of production of bacteria as when strict anaerobic conditions are used.

In another aspect the invention concerns the use of a polypeptide as defined herein, for the preparation of a food product and in particular for dairy product.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of"). Furthermore the indefinite article "a" or "an" does not exclude a plurality. The mere fact that certain measures are recited in mutually different dependent claims does not indicate that a combination of these measures cannot be used to advantage.

The sequences of the present application are as follows:

```
SEQ ID NO: 1:
MLPPMALPSVSWMLLSCLMLLSQVQGEEPQRELPSARIRCPKGSKAYGSH

CYALFLSPKSWTDADLACQKRPSGNLVSVLSGAEGSFVSSLVKSIGNSYS

YVWIGLHDPTQGTEPNGEGWEWSSSDVMNYFAWERNPSTISSPGHCASLS

RSTAFLRWKDYNCNVRLPYVCKFTD
```

-continued

SEQ ID NO: 2:
MEEPQRELPSARIRCPKGSKAYGSHCYALFLSPKSWTDADLACQKRPSGN

LVSVLSGAEGSFVSSLVKSIGNSYSYVWIGLHDPTQGTEPNGEGWEWSSS

DVMNYFAWERNPSTISSPGHCASLSRSTAFLRWKDYNCNVRLPYVCKFTD

SEQ ID NO: 3:
EEPQRELPSARIRCPKGSKAYGSHCYALFLSPKSWTDADLACQKRPSGNL

VSVLSGAEGSFVSSLVKSIGNSYSYVWIGLHDPTQGTEPNGEGWEWSSSD

VMNYFAWERNPSTISSPGHCASLSRSTAFLRWKDYNCNVRLPYVCKFTD

SEQ ID NO: 4:
IRCPKGSKAYGSHCYALFLSPKSWTDADLACQKRPSGNLVSVLSGAEGSF

VSSLVKSIGNSYSYVWIGLHDPTQGTEPNGEGWEWSSSDVMNYFAWERNP

STISSPGHCASLSRSTAFLRWKDYNCNVRLPYVCKFTD

The invention will be further illustrated by the following figures and examples.

FIGURES

FIG. 1: Serum concentrations of human Reg3α and murine Reg3γ in wild-type (WT) and hReg3α-transgenic (hReg3α) mice before (Control) and after (Colitis) treatment with DSS (n=6).

Figure 2:
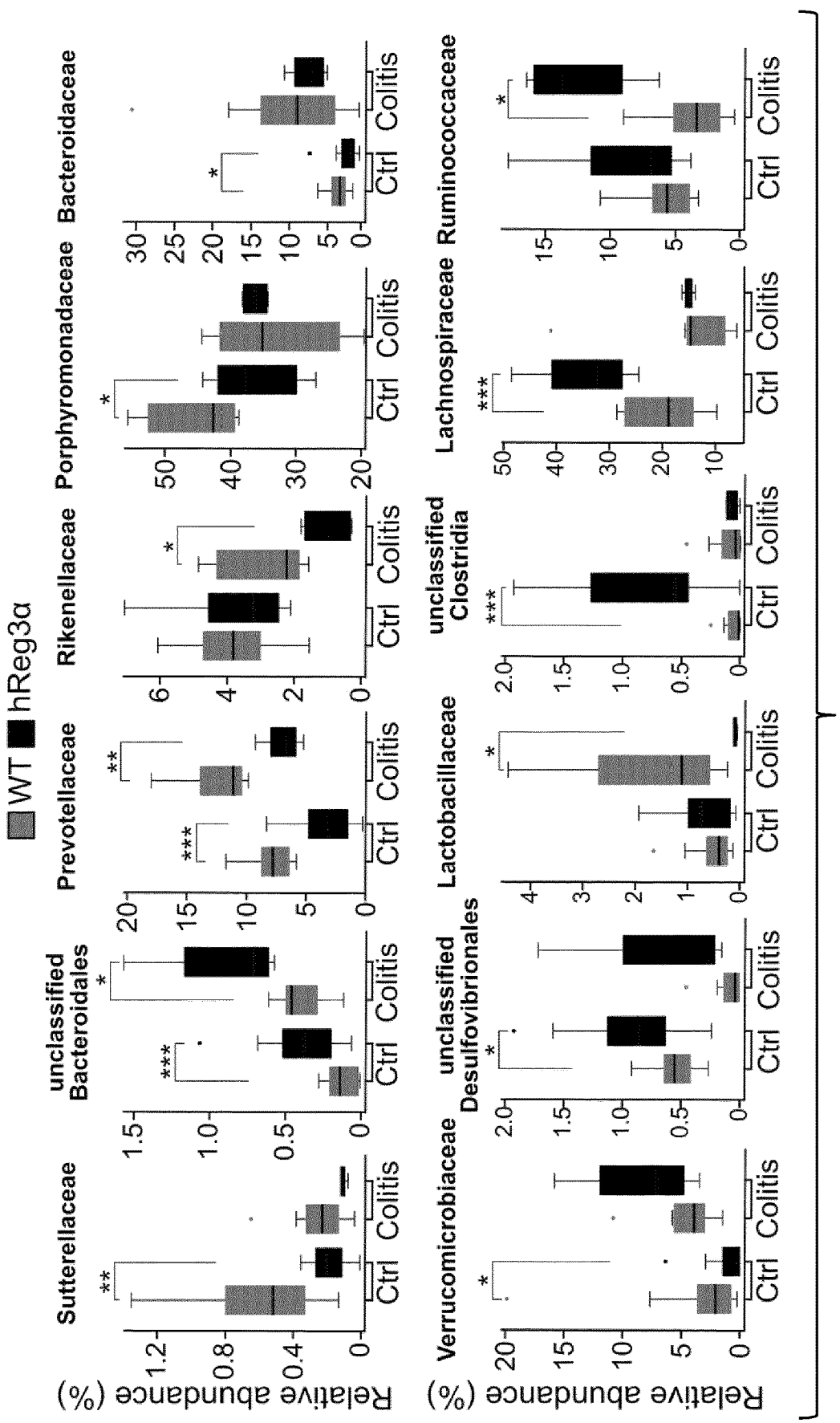

FIG. 2: Relative abundances of bacterial families in the basal state (Ctrl) of the hReg3 α-transgenic (n=5) and WT (n=7) mice and on day 12 after onset of exposure to DSS (Colitis).

Figures 3, 4:
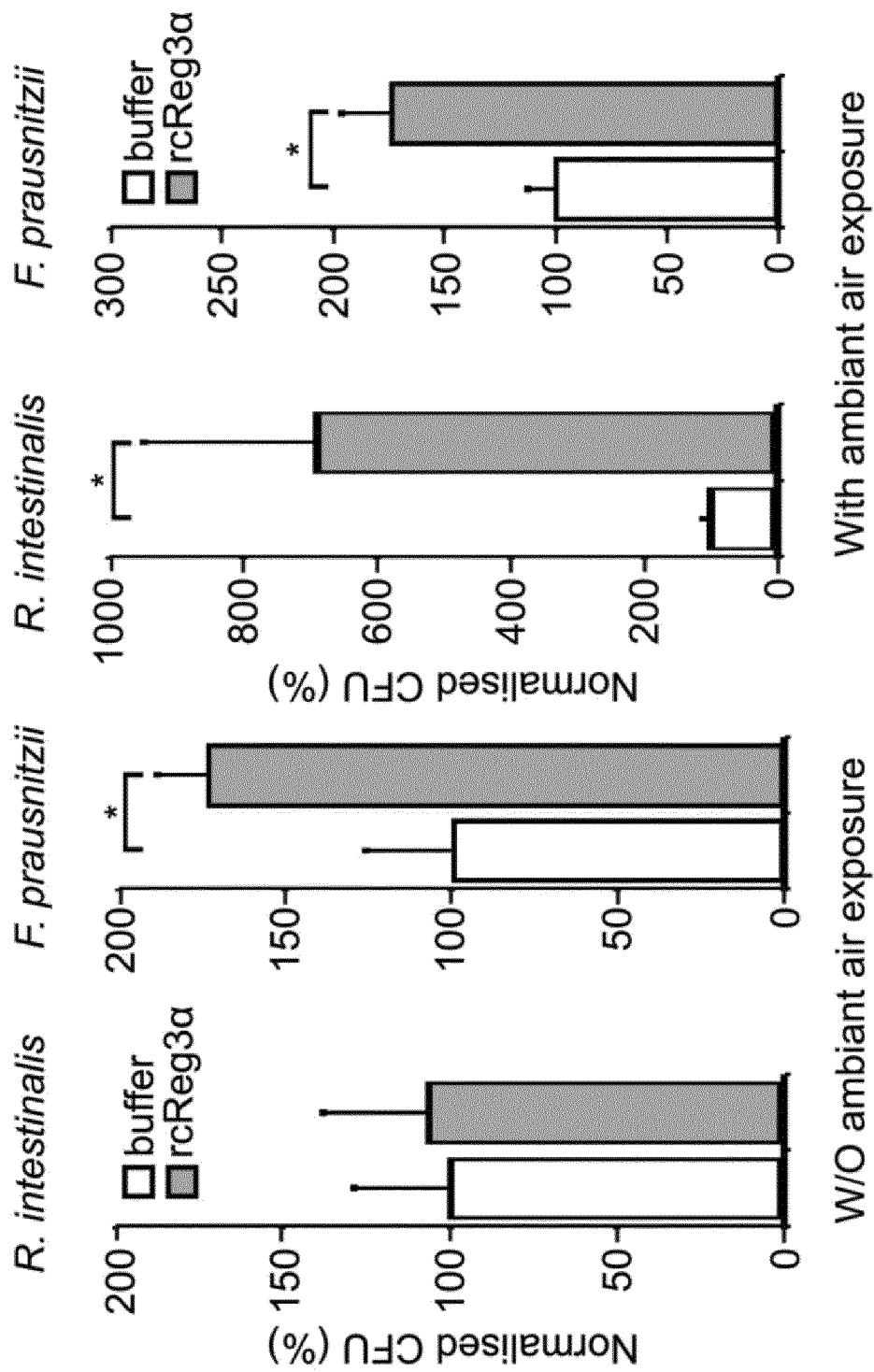

FIG. 3: Normalized CFU (colony-forming unit) numbers of Gram-positive *Roseburia intestinalis* and *Faecalibacterium prausnitzii* in strictly anaerobic cultures.

FIG. 4: Normalized CFU numbers of Gram-positive *Roseburia intestinalis* and *Faecalibacterium prausnitzii* after exposure to ambient air.

In FIGS. 3 and 4, the numbers of CFUs were normalized to the average CFU number measured in control cultures (buffer). Assays were done in quadruplicate in two independent experiments. The data are averages in SEM. The two-sided Wilcoxon rank sum test was performed for analysis. *P<0.05, ***P<0.001.

Figures 5, 6, 7:
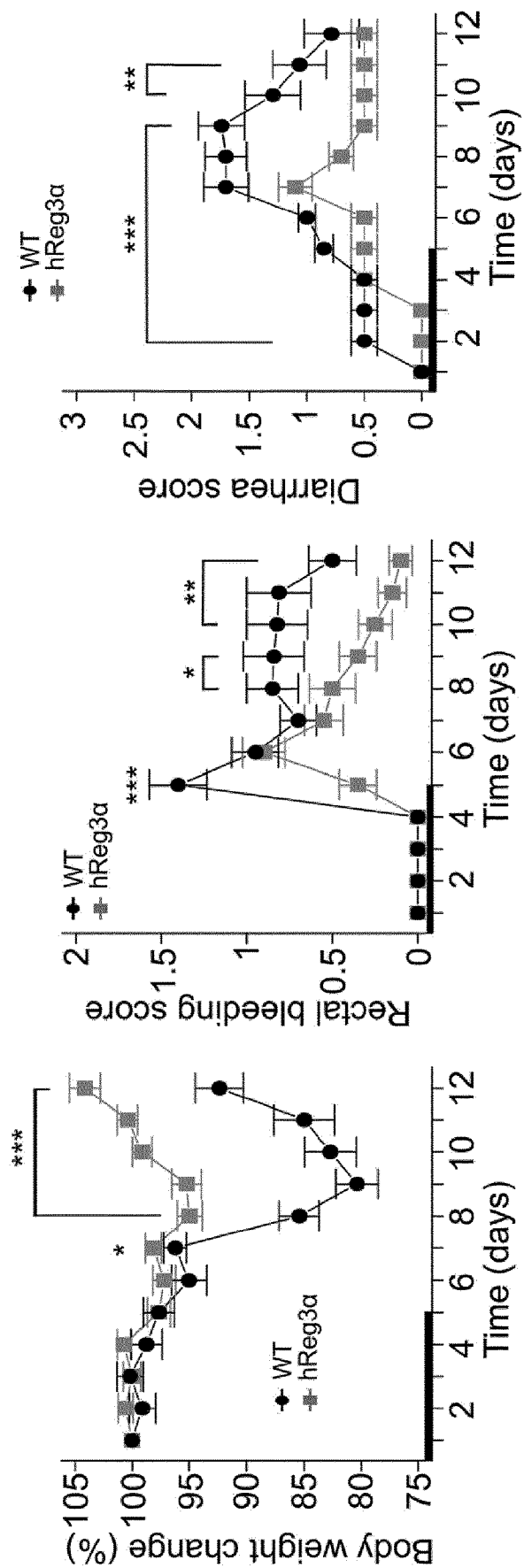

FIG. 5: Evolution of body weight change due to DSS-induced colitis in hReg3α-transgenic (hReg3α) and wild-type (WT) mice (n=20 for each group; 2 independent experiments). Heavy line: 5-day period of DSS administration.

FIG. 6: Evolution of rectal bleeding score due to DSS-induced colitis in hReg3α-transgenic (hReg3α) and wild-type (WT) mice (n=20 for each group; 2 independent experiments). Heavy line: 5-day period of DSS administration.

FIG. 7: Evolution of diarrhea score due to DSS-induced colitis in hReg3α-transgenic (hReg3α) and wild-type (WT) mice (n=20 for each group; 2 independent experiments). Heavy line: 5-day period of DSS administration.

Figure 8:
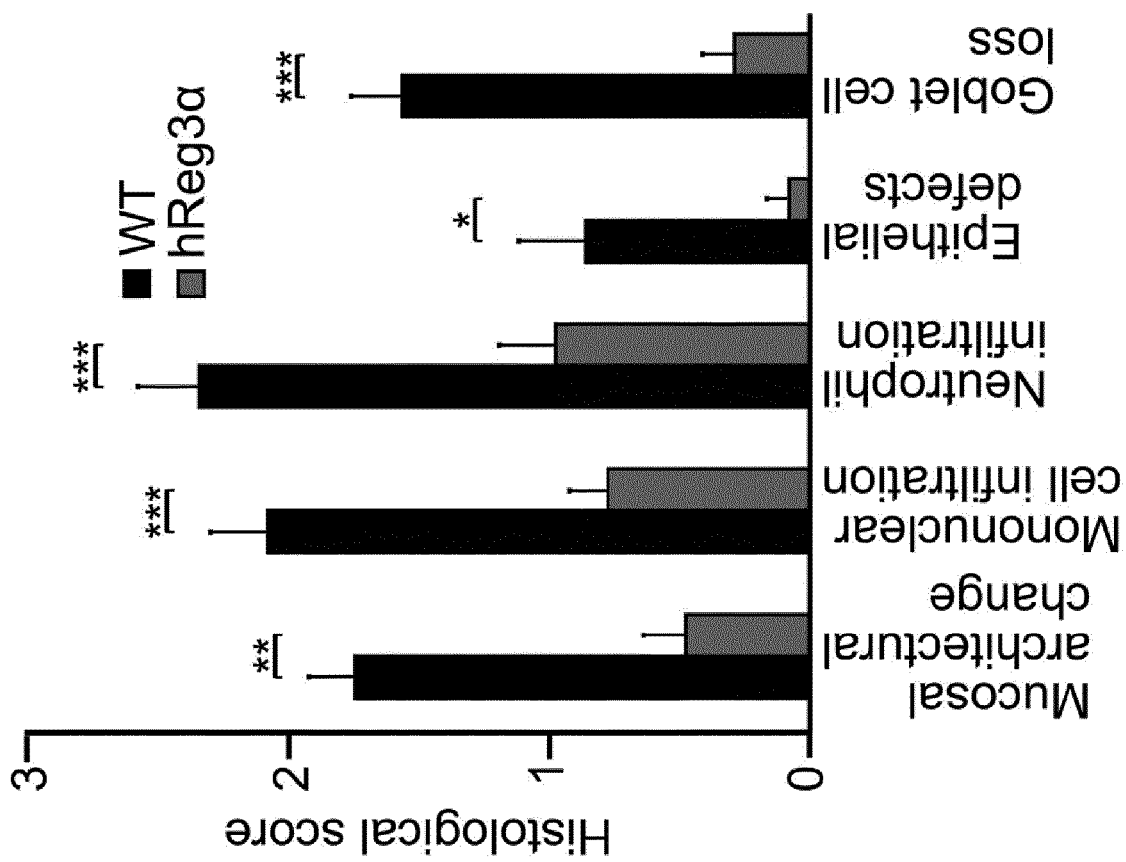

FIG. 8: Histological assessment of gut epithelium (n=14 for each group).

Figure 9:
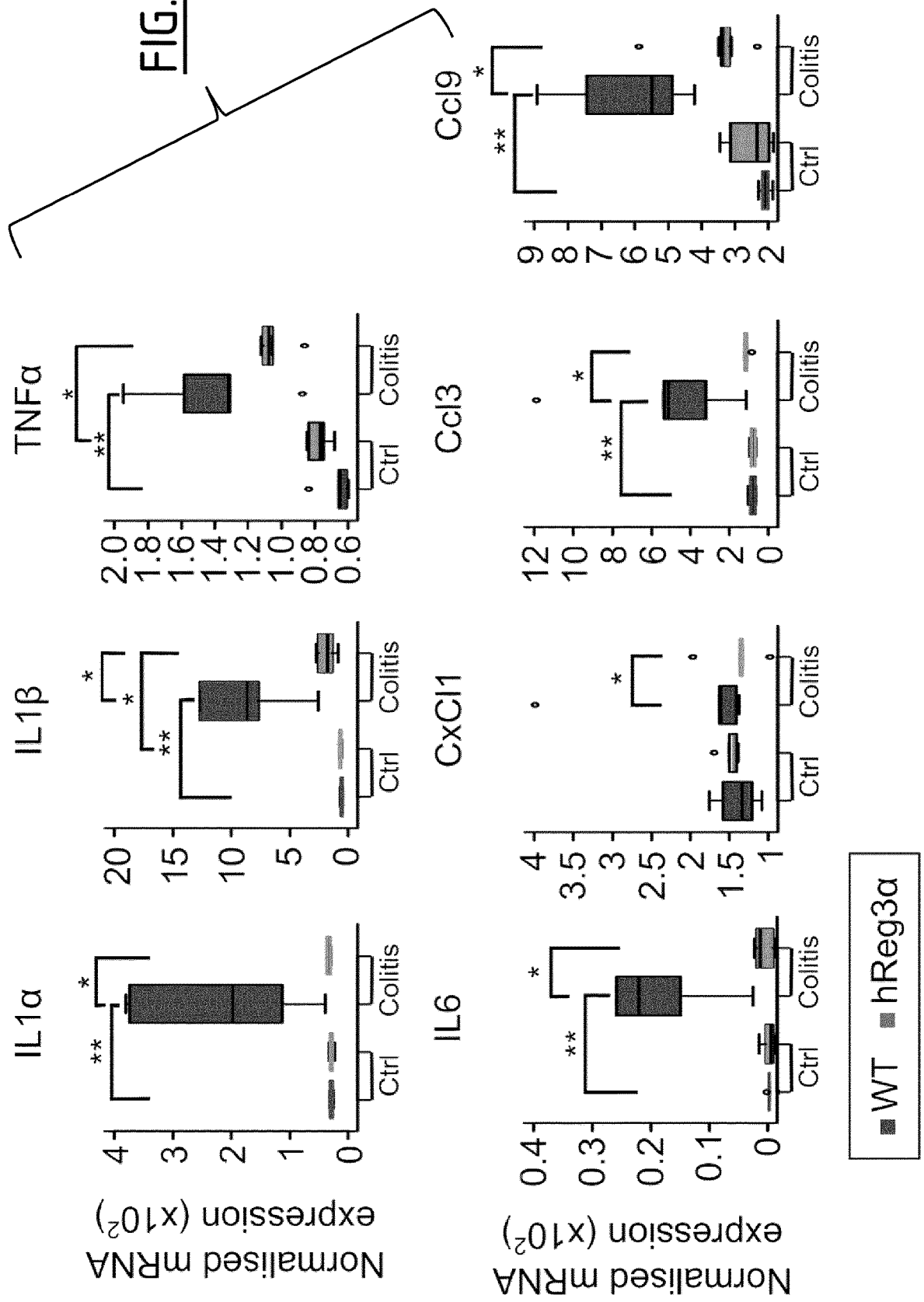

FIG. 9: mRNA expression level of the indicated inflammatory markers in colonic epithelial cells of WT and hReg3α-transgenic mice (n=5). The data are means±SEM. The two-sided Wilcoxon rank sum test was performed for analysis. *P<0.05, P<0.01, *P<0.001.

Figure 10:
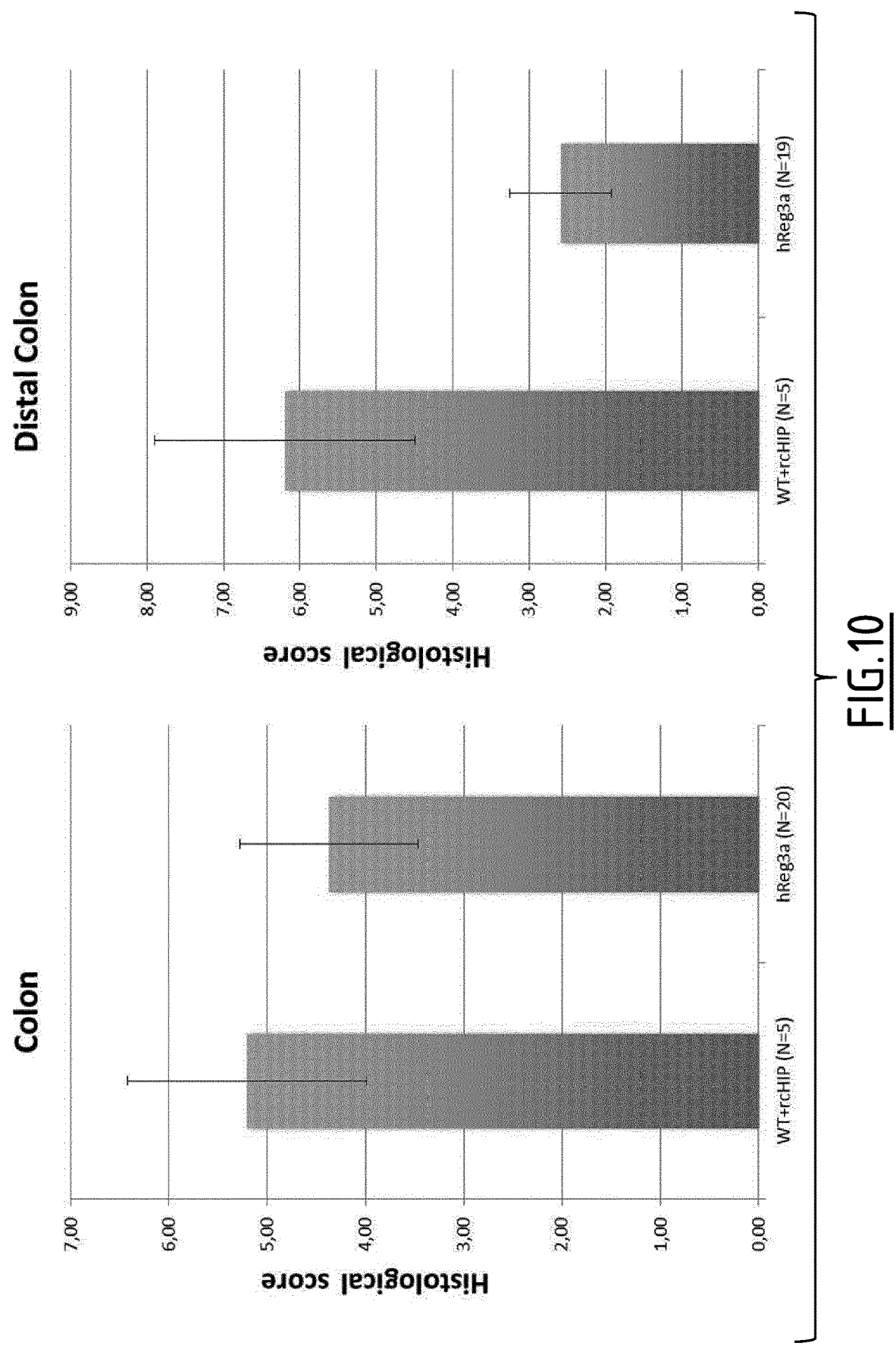

FIG. 10: Histological assessment of colon and distal colon of mice during DSS-induced colitis. WT+rcHIP correspond to WT mice treated with 4.2 µg recombinant hReg3α (rc-hReg3α)/g mice/day administered intravenously. hReg3α correspond to hReg3α-transgenic mice. The data are means±SEM. Histological score is based on the evaluation of the mucosal architectural change, mononuclear cell infiltration, neutrophil infiltration epithelial defects and Goblet cell loss.

Figure 11:
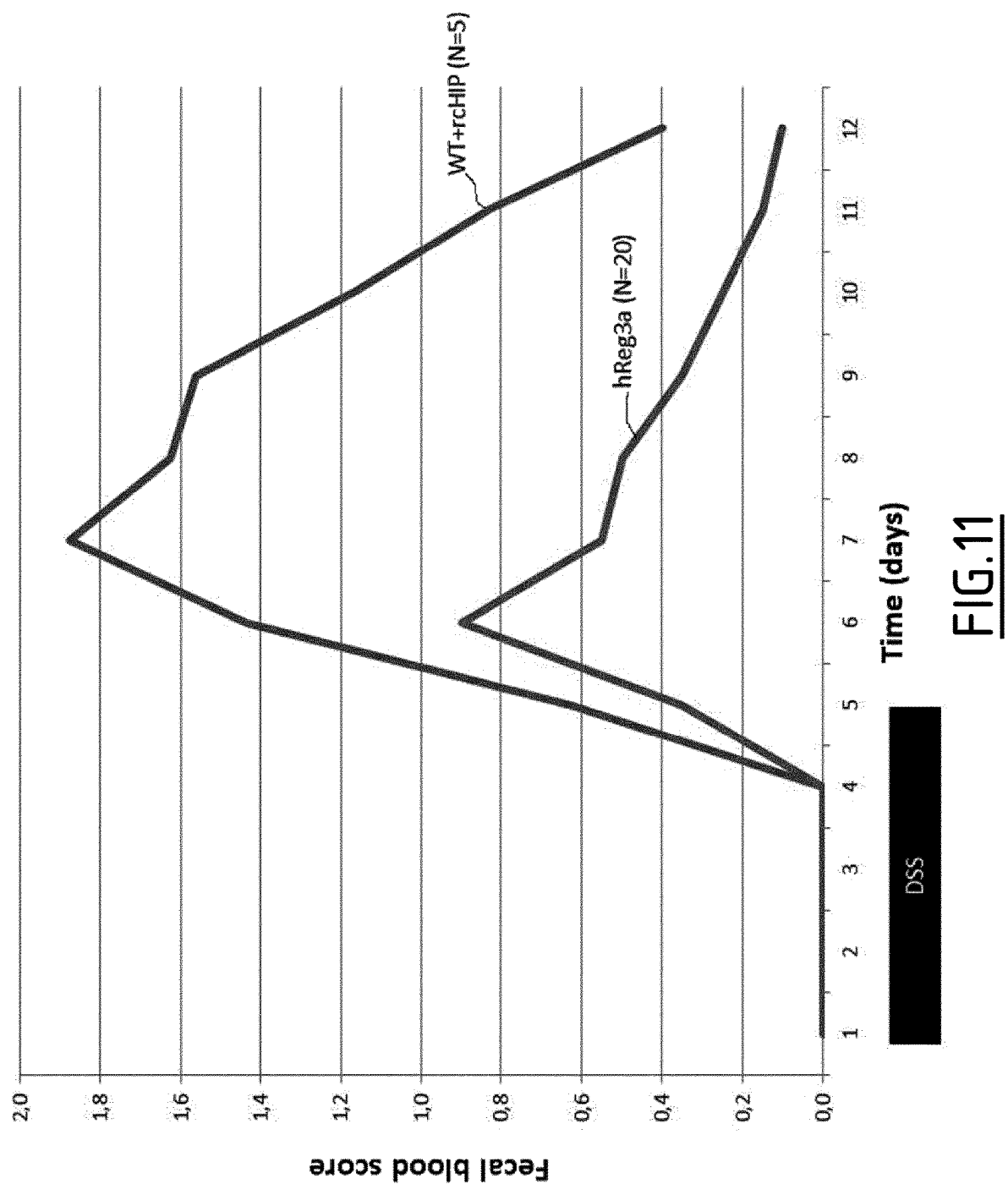

FIG. 11: Evolution of fecal blood score due to DSS-induced colitis in hReg3α-transgenic (hReg3α) and WT+rcHIP mice. Heavy line: 5-day period of DSS administration.

Figure 12:
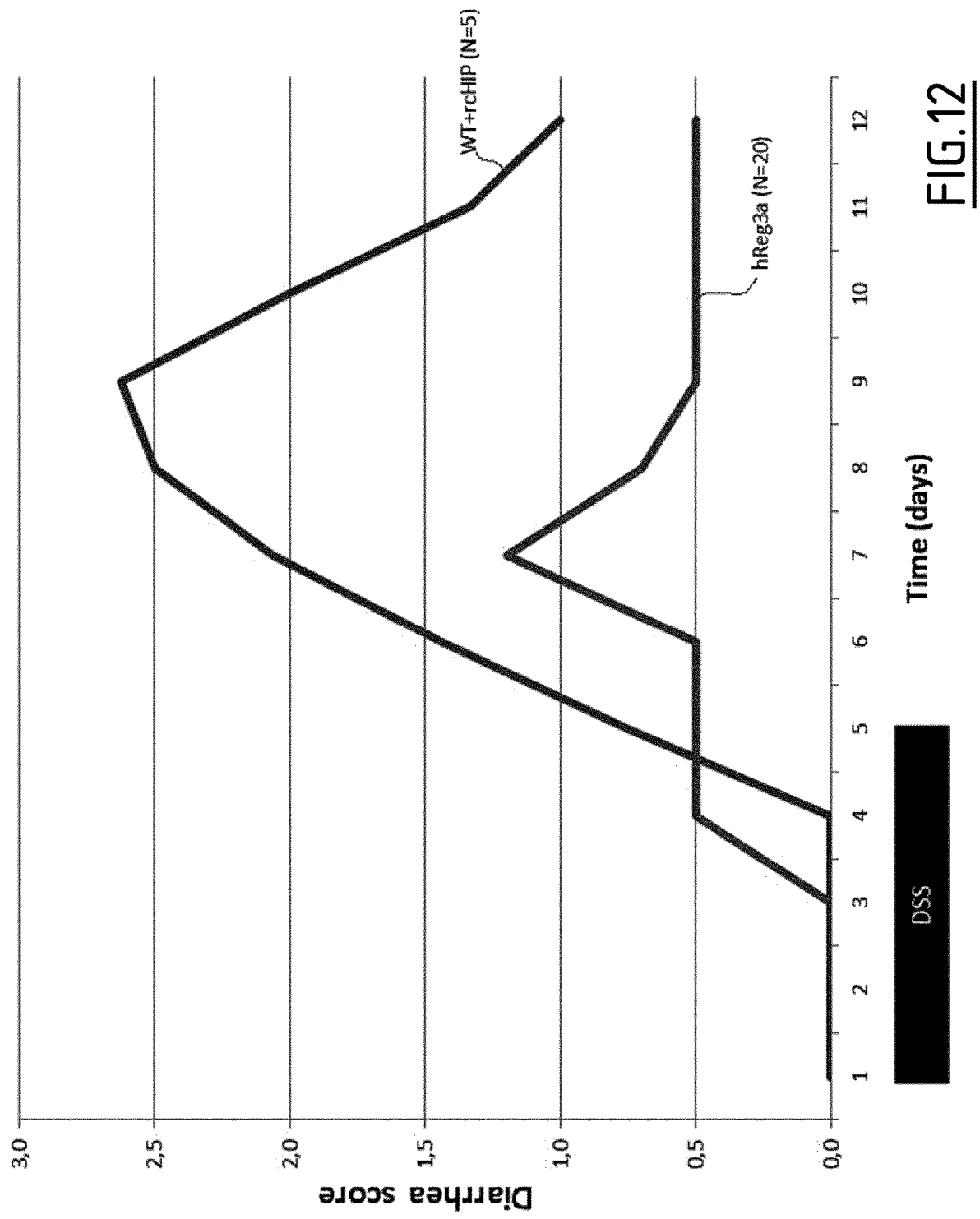

FIG. 12: Evolution of diarrhea score due to DSS-induced colitis in hReg3α-transgenic (hReg3α) and WT+rcHIP mice. Heavy line: 5-day period of DSS administration.

Figure 13:
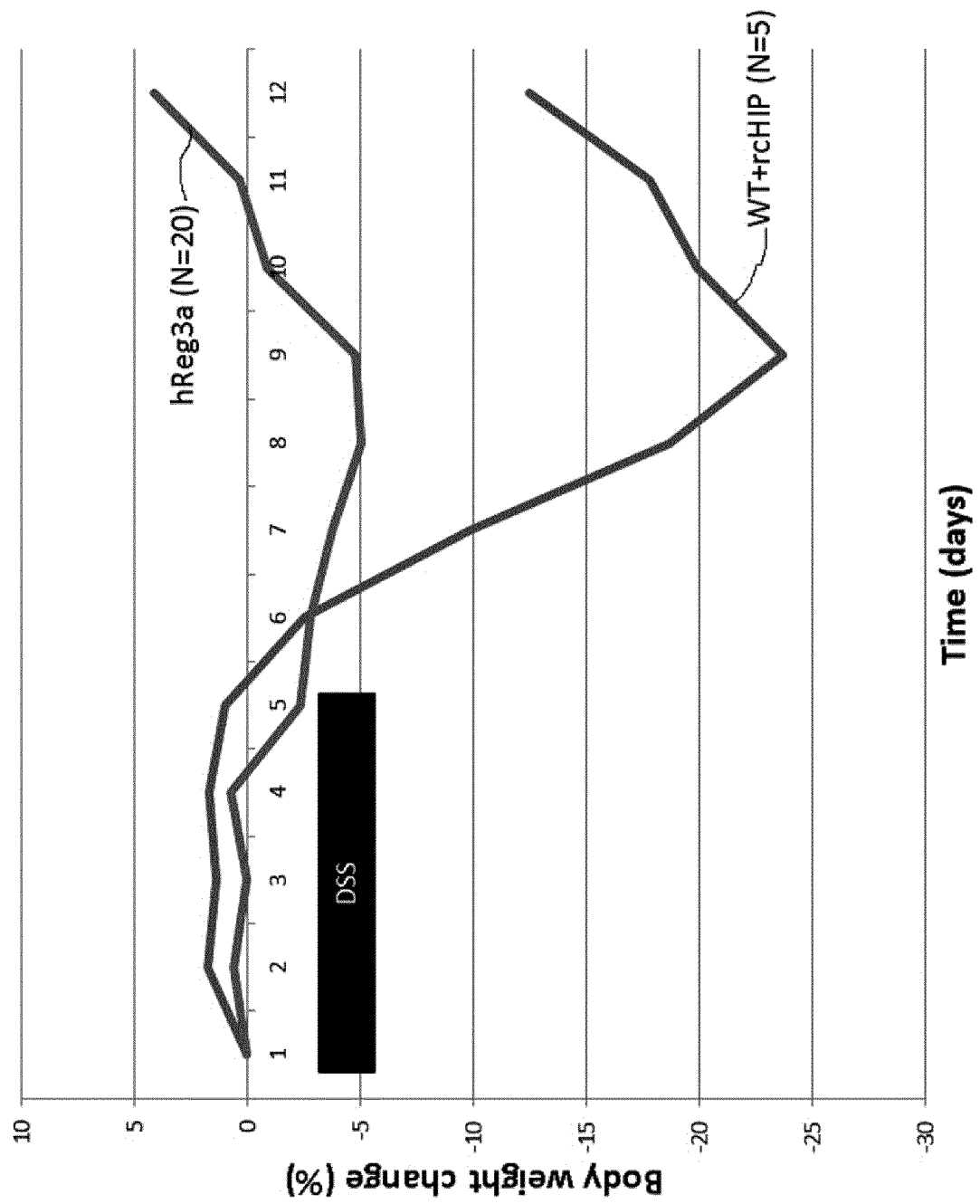

FIG. 13: Evolution of body weight change due to DSS-induced colitis in hReg3α-transgenic (hReg3α) and WT+rcHIP mice. Heavy line: 5-day period of DSS administration.

Figure 14:
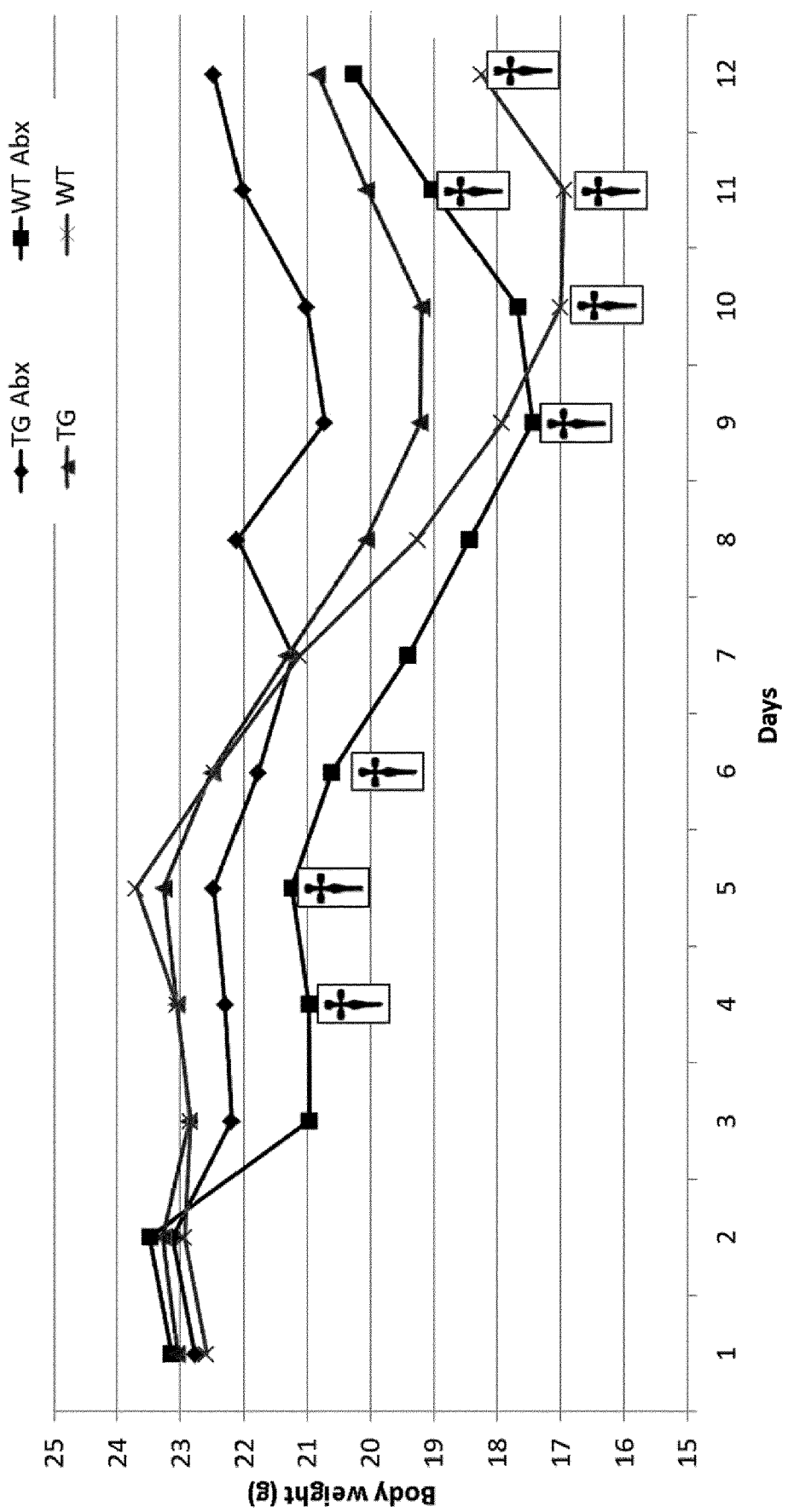

FIG. 14: Evolution of body weight change due to DSS-induced colitis in TG Abx, WT Abx, TG and WT mice.

TG mice correspond to hReg3α-transgenic mice which were not treated with antibiotics. WT mice correspond to wild-type mice which were not treated with antibiotics. TG Abx correspond to hReg3α-transgenic mice having being treated with antibiotics. WT Abx mice correspond to WT mice having being treated with antibiotics.

Death of a mouse is symbolized by cross on the graphic.

Figure 15:
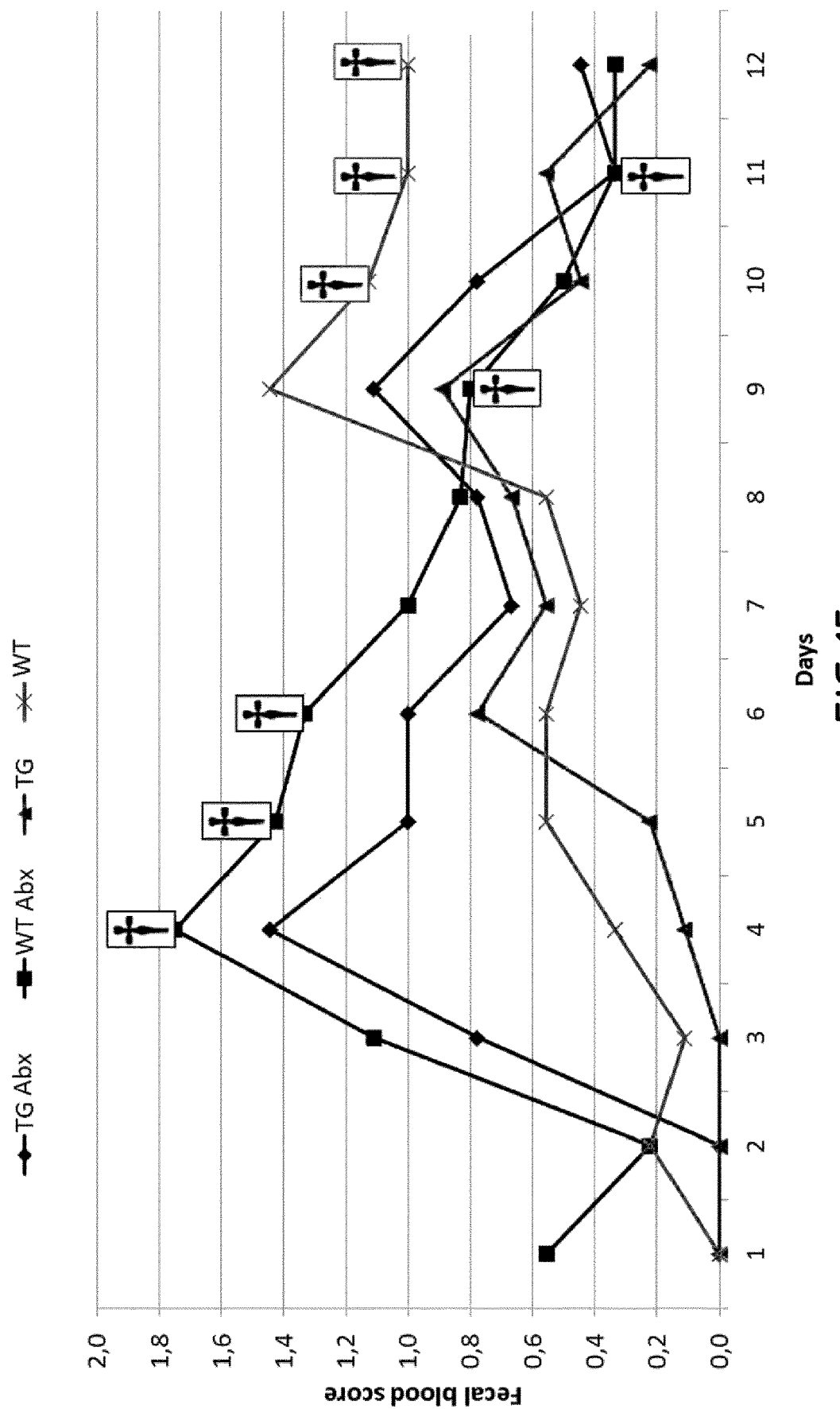

FIG. 15: Evolution of fecal blood score due to DSS-induced colitis in TG Abx, WT Abx, TG and WT mice.

Death of a mouse is symbolized by cross on the graphic.

Figure 16:
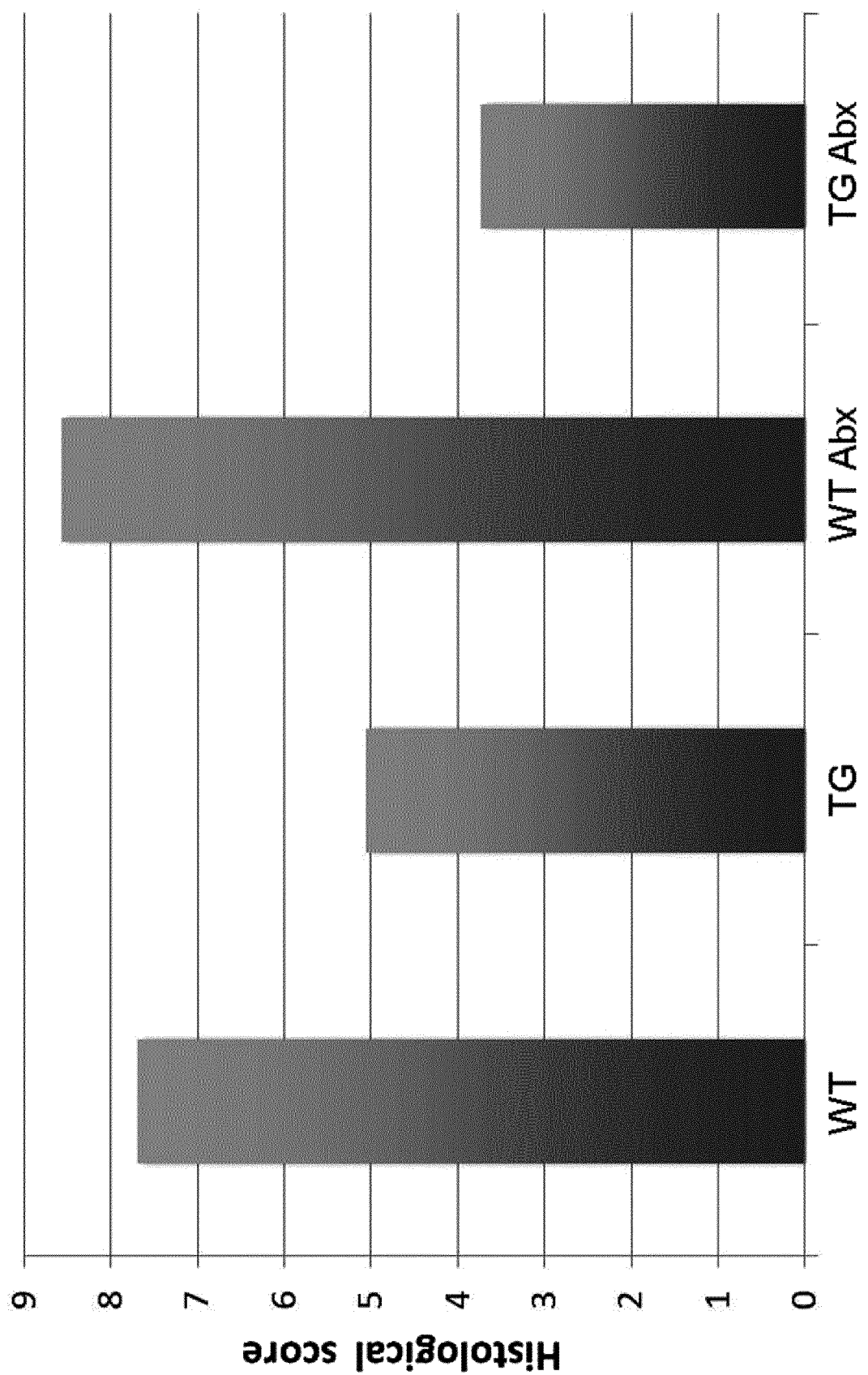

FIG. 16: Histological assessment of the distal colon of mice during DSS-induced colitis in TG Abx, WT Abx, TG and WT mice.

EXAMPLES

Example 1: Human Reg3α Delivered into the Gut Lumen Shifts the Gut Microbiota Composition in Hepatocyte-Targeted Reg3α Transgenic Mice We studied the effects of human Reg3α (hReg3α) on the composition of the gut microbiota and gut barrier integrity in mice transgenic for hReg3α under homeostatic and inflammatory conditions. Inflammation was induced by oral absorption of dextran sodium sulphate (DSS). To prevent degradation of the hReg3α protein by acid and luminal proteases in the upper GIT, we used previously generated homozygous transgenic C57BL/6 mice expressing hReg3α in hepatocytes under the control of the mouse albumin gene promoter and showed that, in these mice, the hReg3α protein flowed into bile ducts and into the gastrointestinal tract (GIT) lumen. Transgenic hepatocytes secreted hReg3α into blood vessels through the basolateral membranes, and into bile canaliculi through the apical membranes.

The expression levels of endogenous Reg3β and Reg3γ in the blood and colon tissue were negligible in the basal state of wild-type (WT) mice and high in DSS-treated WT mice, as expected (FIG. 1). In hReg3α-transgenic mice, a similar high serum level of hReg3α was found in the basal and inflammatory states (FIG. 1). This level was of the same order of magnitude as that of the endogenous Reg3 in DSS-treated WT mice. The colon expression levels of the endogenous Reg3 mRNAs were negligible in both the basal and inflammatory states of hReg3α-transgenic mice. In other words, hReg3α-transgenic mice did not display any up-regulation of Reg3β or Reg3γ during DSS-induced colitis (perhaps because they were retro-controlled by the over-expressed hReg3α), implying that Reg3β and Reg3γ played a negligible part in the disease phenotype and gut microbiota composition exhibited by hReg3α-transgenic mice.

We next analysed the composition of the faecal microbiota in healthy and DSS-treated hReg3α-transgenic mice using MiSeq 16S rDNA gene sequencing. Control WT and hReg3α-transgenic mice were bred and processed under the same conditions. Principal component analysis (PCA) revealed two clearly separate clusters for hReg3α-transgenic and WT mice at the family level both before (P=0.001) and after (P=0.039) exposure to DSS. Twelve bacterial families displayed significant differences in their relative abundance between hReg3α-transgenic and WT mice in both the basal and inflammatory states (FIG. 2). In the basal state of hReg3α-transgenic mice, Sutterellaceae (phylum Proteobacteria), Prevotellaceae, Porphyromonadaceae and Bacteroidaceae (phylum Bacteroidetes) were under-represented, while Lachnospiraceae and unclassified Clostridia (phylum Firmicutes) were over-represented. The same shifts in microbial composition were also found at the genus level. In the inflammatory state, WT mice displayed an increase in Prevotellaceae and Bacteroidaceae, and a decrease in all the other families mentioned above. hReg3α-transgenic mice behaved similarly, except for Prevotellaceae, whose level remained low, and Ruminococcaceae (order Clostridiales), whose level rose dramatically (FIG. 2).

The gut microbiota composition we observed in homozygous transgenic (hReg3α-TG+/+) mice might be due to the Reg3α transgene or an extra-genetic effect. To solve this issue, we studied the time evolution of an initially WT microbiota in heterozygous transgenic (hReg3α-TG+/−) pups born to WT mothers. The faecal microbiomes of 15 hReg3α-TG+/− pups from three different litters and cages were sequenced at the ages of 9 and 12 weeks and compared to those of their WT dams (n=3) and those of unrelated WT mice of similar ages (n=11). The faecal microbiomes of twelve hReg3α-TG+/+ mice were also analysed for comparison. PCA (Principal component analysis) plots at the family level showed that the microbiota from hReg3α-TG+/− mice were grouped in between those from (maternal and unrelated) WT and hReg3α-TG+/+ mice at 9 weeks (P<0.01 for hReg3α-TG+/− vs WT and hReg3α-TG+/− vs hReg3α-TG+/+) and moved close to those from hReg3α-TG+/+ mice during the next three weeks (P<0.001 for hReg3α-TG+/− vs WT; P>0.05 for hReg3α-TG+/− vs hReg3α-TG+/+). The microbiota composition shift of the hReg3α-TG+/− mice mostly consisted of a decrease in Prevotellaceae, Sutterellaceae and Verrucomicrobiaceae and an increase in Lachnospiraceae and Ruminococcaceae, to reach levels comparable to those of hReg3α-TG+/+ mice after 12 weeks. Thus the WT microbiota of the heterozygous newborns evolved toward a transgenic-positive microbiota in a few months, which means that the Reg3α transgene effect superseded the maternal legacy.

Reg3α Increases the Viability of Some Highly Oxygen-Sensitive Clostridia

The shift in microbiota composition in hReg3α-transgenic mice corresponded to a large increase in the ratio between Gram-positive and Gram-negative bacteria, difficult to reconcile with the reported selective anti-Gram-positive bactericidal activity of hReg3α. We conjectured that the antioxidant activity of hReg3α was the key factor in shifting the intestinal microbial ecology in hReg3α-transgenic mice. The mechanism at play would be a selection pressure exerted by hReg3α in favour of strict anaerobic Gram-positive bacteria, as are some Clostridia. To substantiate this view, we tested the antioxidant efficiency of a full-length recombinant human Reg3α protein (rcReg3α) in prokaryote cells in vitro. The recombinant protein we used is chemically and biologically active in terms of anti-inflammatory properties in eukaryotic cells and carbohydrate binding selectivity. We first cultured *Enterococcus faecalis*, a Gram-positive enteric commensal bacterium, stressed with a ROS generator (paraquat) during the exponential phase of growth. Exposure to 200 mM paraquat had a strong bactericidal effect on *E. faecalis*. The addition of 10 μM rcReg3α restored the exponential growth of *E. faecalis*, suggesting that the ROS generated by paraquat were effectively reduced in the presence of rcReg3α. This was demonstrated by flow cytometry measurements using the ROS-specific fluorescent probe H2-DCFDA and propidium iodide DNA staining. We found some bacterial aggregation, but no bactericidal effect of rcReg3α on *E. faecalis*, at variance with previous reports. This discrepancy may rely on the bacterial strain, but note that an absence of bactericidal activity of Reg3α would be consistent with the enrichment of Gram-positive bacteria we observed in the gut microbiota of transgenic mice.

We next turned to cultures of two well-documented extremely oxygen sensitive Gram-positive bacteria species, *Roseburia intestinalis* (Lachnospiraceae, *Clostridium* Cluster XIVa) and *Faecalibacterium prausnitzii* (Ruminococcaceae, *Clostridium* Cluster IV), which are major producers of butyrate and anti-inflammatory compounds in the human gut microbiota whose abundance is dramatically reduced during IBD. *R. intestinalis* is known to survive for less than 2 min when exposed to air on the surface of agar plates. *F. prausnitzii* is even more sensitive to air exposure than *R. intestinalis*, grows slowly under anaerobic conditions, and becomes micro-aerotolerant in the presence of antioxidants through mechanisms of electron transfer to oxygen. We performed anaerobic cultures of *R. intestinalis* and *F. prausnitzii* followed, or not, by a 5-min exposure to ambient air. We found that rcReg3α had a significant growth-promoting effect on *F. prausnitzii* under strict anaerobic conditions and a survival effect on both bacteria after exposure to oxygen (FIGS. 3 and 4). The centrifugation of *F. prausnitzii* anaerobic cultures incubated with rcReg3α for 24 h, followed by anti-Reg3α-immunoblotting, showed that a 15-kDa rcReg3α co-sedimented with bacterial aggregates. Slide-mounted imaging showed that *F. prausnitzii* incubated with rcReg3α survived, whereas control cultures were completely lysed, after 2 h of exposure to ambient air. These findings establish that rcReg3α exerts a potent antioxidant activity on prokaryotic cells and is capable of increasing the viability and growth of some extremely oxygen-sensitive commensal Clostridia. They support our assumption that the ROS scavenger activity of hReg3α decisively contributes to the shift of gut microbiota observed in hReg3α-transgenic mice.

hReg3α-Transgenic Mice are Fully Resistant to DSS-Induced Colitis

The dysbiotic microbiota of patients with IBD is mostly characterized by an increase in Sutterellaceae, Prevotellaceae, and Enterobacteriaceae (phylum Proteobacteria) and a decrease in Ruminococcaceae and Lachnospiraceae (which include the principal butyrate-producing symbionts). Similar shifts in the composition of the gut microbiota are also associated with colitis in genetically susceptible mouse models. The fact that more or less reverse shifts occur in the gut microbiota of hReg3α-transgenic mice suggests that a microbiota shaped by hReg3α might have a beneficial impact on health.

To test this idea, we studied the response to induced colitis in hReg3α-transgenic mice, and then performed cohousing and faecal transplantation experiments. Homozygous hReg3α-transgenic mice received oral administrations of 3% DSS for 5 days followed by normal drinking water for 7 days. Control groups of WT mice were bred and processed under the same conditions. Body weight changes, stool consistency and bleeding scores and survival rate were monitored over time. Histopathological features were scored on day 12. Strikingly, DSS-treated hReg3α-transgenic mice displayed only a very few signs of acute colitis. They had reduced weight loss, diarrhea and rectal bleeding compared to WT mice and had a 100% survival rate on day 12 compared to 70% in WT mice (FIGS. 5-7). Their colons displayed fewer barrier defects and less Goblet cell loss and inflammatory cell infiltration than those of WT mice (FIG. 8). Twelve-week-old heterozygous hReg3α-transgenic mice born to WT mothers were also exposed to DSS and we found that they exhibited a relatively benign colitis, consistent with the fact that their gut microbiota was similar in composition, and thus functionality, to those of homozygous transgenic mice. We ensured that the hReg3α lectin did not interact with dextran in vitro, in agreement with previous reports, and that, therefore, the observed phenotype could not be attributed to a direct blocking of DSS toxicity by hReg3α. Positron emission tomography (PET) imaging with 2-[18F]fluoro-2-deoxy-D-glucose ([18F]FDG), a tracer for abnormally high glucose metabolism in inflammatory areas, was used to quantify intestinal inflammation. Colonic [18F]FDG uptake increased over time in DSS-treated WT mice whereas it remained weak (i.e. comparable to that seen in non-treated mice) in hReg3α-transgenic mice (P=0.013 over the d7-d12 time period). The severity of DSS-induced colitis was also assessed by measuring the colonic expression levels of inflammatory markers (IL1α, IL1β, TNFα, IL6, CXCL1, CCL3, CCL9). Most of them showed a significant increase upon DSS administration in WT mice, and not in hReg3α-transgenic mice (FIG. 9). We studied the integrity of the gut mucosal barrier in healthy and DSS-treated hReg3α-transgenic mice using immunostaining for Muc2 mucin and 16S rRNA FISH, transcriptome profiling and gene set enrichment analysis (GSEA) with the KEGG and Reactome databases. In the basal state, the optical microscope images of mucosal barriers in hReg3α-transgenic and WT mice were similar. However, several pathways related to the intestinal barrier, including modulators of cell-matrix interactions and mucin O-glycosylation, were upregulated in hReg3α-transgenic mice. During intestinal inflammation, the colon mucosal barrier remained intact over considerable areas in hReg3α-transgenic mice, whereas it was largely disrupted in WT mice, leading to bacterial colonization across the epithelium. The functional robustness of the mucosal barrier in hReg3α-transgenic mice compared to WT mice was further highlighted as follows. An up-regulation of some tight-junction genes involved in the regulation of cell-cell interactions was observed. An increase in O-glycosylation of epithelial mucins was revealed by wheat germ agglutinin (WGA) immunoblotting. The level of bacterial translocation in mesenteric lymph nodes remained low, as shown by 16S rRNA FISH analysis. An unsupervised analysis of transcriptomic profiles revealed a down-regulation of the gene set related to lipopolysaccharide endotoxin (LPS) pathway activation in DSS-treated hReg3α-transgenic mice, whose profiles clustered with those of non DSS-treated mice. Consistent with this, the increase in inflammation-associated serum markers (LPS, soluble CD14) remained very small in these mice during intestinal inflammation. Finally, the concentration of malondialdehyde (MDA), a biomarker of oxidative stress, in the colon tissue was substantially reduced in DSS-treated hReg3α-transgenic, compared to WT, mice, providing in vivo evidence that the gut epithelium greatly benefited from the antioxidant properties of hReg3α during acute colitis.

The Anti-Inflammatory Properties of Gut Microbiota Shaped by hReg3α Promote Survival to DSS-Induced Colitis in Colonized Wild-Type Mice To assess the protective action of hReg3α-shaped microbiota against colitis, we transferred faecal microbiota from hReg3α-transgenic mice to WT mice by means of cohousing. Three-week-old weaned WT mice were cohoused with age-matched hReg3α-transgenic mice for 8 weeks and then submitted to treatment with DSS. Control groups consisted of WT mice housed alone. At the end of the cohousing period, cohoused WT (CoH-WT) mice displayed a significant shift in gut microbiota composition towards a hReg3α-transgenic profile at the bacteria family level and a clear alleviation of DSS-induced colitis in terms of stool consistency and bleeding, gut barrier integrity and survival rate.

Next, we colonized germ-free C57BL/6 mice with a faecal microbiota from hReg3α-transgenic or WT mice for 3 weeks. At the end of this period, the faecal microbiota was analysed by sequencing (Day 0) and then the DSS treatment of the colonized mice started. The microbiota of colonized hReg3α-transgenic (ExGF-TG) and WT (ExGF-WT) mice at D0 had somewhat drifted from their respective inocula. Nevertheless, the microbiota of ExGF-TG mice still harboured the same predominent bacterial communities as the inoculum, albeit with different relative abundance values, and remained far from that of ExGF-WT mice. Upon DSS treatment, ExGF-TG mice exhibited a complete colitis survival, whereas 37% of the ExGF-WT mice died, in spite of transient signs of colitis, especially, diarrhea and barrier defects. This was associated with a reduced inflammatory response in terms of TLR4 signalling activation and expression levels of colonic inflammatory markers in the colon, and LPS-induced endotoxemia.

Overall, these results demonstrate a transmissible pro-survival action of the microbiota shaped by hReg3α probably due to a reduced inflammatory response in the gut epithelium and less systemic dissemination of gram-negative LPS. This is consistent with the depletion of potentially aggressive Gram-negative bacteria we observed in the gut microbiota shaped by hReg3α. The fact that clinical and histological signs of colitis in CoH-WT and ExGF-TG mice were partly reduced while they were fully suppressed in hReg3α-transgenic mice suggests that, in the latter, a direct interaction between over-expressed hReg3α and the host contributed to the maintenance of gut barrier homeostasis, in addition to the anti-inflammatory effects of the gut microbiota shaped by hReg3α.

Discussion

It is generally accepted that enteric innate immune molecules play an important role in gut barrier function and gut microbiota homeostasis through their pleiotropic activities. It is also widely believed that an impairment of their functional expression is a key contributory factor to chronic inflammatory intestinal because it destabilizes the symbiotic interplay between gut microbes and the gut epithelial barrier. However, whether their manipulation might help to preserve host-microbiota homeostasis and thus prevent intestinal inflammation still remained to be established. In this study, we showed that an increase in the luminal concentration of the hReg3α lectin in transgenic mice induced significant changes to the composition of the gut microbiota, and dramatically improved host resistance to intestinal inflammation. In fact, hReg3α-transgenic mice exposed to DSS exhibited very few signs of colitis, retained a tight mucosal barrier and achieved complete survival. We found that the inflammatory response and the oxidative stress in the colon epithelium was much reduced in DSS-treated hReg3α-transgenic, compared to WT, mice, indicating that hReg3α exerted a potent antioxidant activity on intestinal epithelial cells during colitis. Our in vitro studies also showed that the ROS scavenging activity of a recombinant human Reg3α (rcReg3α) acted on prokaryote cells, in particular, by promoting the survival of highly oxygen sensitive bacteria.

The microbial changes exhibited by homozygous hReg3α-transgenic mice in homeostatic as well as inflammatory conditions mainly concerned an enrichment of Clostridiales (Ruminococcaceae, Lachnospiraceae) and a depletion of Bacteroidetes (Prevotellaceae). Mice heterozygous for hReg3α that harbored a wild-type maternal microbiota at birth progressively acquired a gut microbiota composition close to that of homozygous hReg3α-transgenic mice demonstrating the capability of hReg3α to shape the gut microbiota—and then exhibited a resistance to colitis similar to that of homozygous mice. The transfer of a hReg3α-shaped microbiota to wild-type mice exposed to DSS resulted in a less severe disease, a less pronounced dissemination of LPS into the blood and an increased survival rate, establishing the beneficial nature of the shift in microbiota composition induced by hReg3α. However, the fact that the phenotypic resistance was not fully transmitted by transfer experiments suggests that hReg3α acted also by other ways in hReg3α-transgenic mice, most probably, through a direct antioxidant mucosal effect. A systemic anticolitogenic effect can be discarded since intravenous administration of rcReg3α did not improve DSS-induced colitis in WT mice. Thus, hReg3α provides protection against oxidative stress for both the intestinal epithelium and the commensal communities that form the gut microbiota. Future studies will be necessary to determine the location of the sites involved in the ROS scavenging activity of hReg3α.

As there are major differences in oxygen tolerance between gut bacteria, the broad-spectrum antioxidant activity of hReg3α may arguably change the balance between the different bacterial communities. Our results suggest that, in our mouse model, some highly oxygen-sensitive commensal bacteria were responsive to the presence of an exogenous antioxidant such as hReg3α, which conferred on them a selective advantage over aerotolerant anaerobic ones, i.e. those capable of developing their own effective adaptive response to oxygen toxicity. In this hypothesis, hReg3α would shape the gut microbiota in the steady state through its antioxidant activity against the environmental stressors existing in the gut of healthy mice and would continue to exert this effect under inflammation and oxidative stress. This view is supported by the fact that Reg3α enhanced the growth of highly oxygen-sensitive commensals belonging to the Clostridiales order (Ruminococcaceae, Lachnospiraceae). An enrichment of such symbionts, which produce anti-inflammatory molecules, may trigger a virtuous process by improving gut barrier function, which feeds back into maintaining a symbiotic bacterial balance due to a reduction in ROS production. Conversely, an increase in Gram-negative commensal bacteria may trigger macrophage activation, increase ROS production, and amplify mucosal injuries and dysbiosis in favour of aerotolerant commensals. Our results suggest that the pressure exerted by hReg3α on the gut microbiota triggers such a virtuous shift in composition and functionality.

From a clinical viewpoint, our findings suggest that a modulation of the intraluminal concentration of Reg3α, for instance via a colon-targeted delivery of a recombinant Reg3α, may be a valuable approach to attenuate intestinal inflammation through a gut microbiota reshaping. Regarding the potential benefits to patients, such an approach would be a more physiological and nontoxic strategy for the treatment of inflammatory outbreaks than the available therapies, including faecal transplantation. Moreover, it might be most successful in the early stages of the inflammatory process or even before the onset of inflammation and could therefore be useful for the maintenance of medically- or surgically-induced remission and even the prevention of IBD in high-risk individuals.

Example 2

Intravenous Administration of rcReg3α Did not Improve DSS-Induced Colitis in WT Mice Contrary to hReg3α Transgenic Mice We studied the effects of intravenous administration of 4.2 µg of recombinant human Reg3α (rcReg3α) per day in WT mice under inflammatory conditions. Inflammation was induced by oral absorption of dextran sodium sulphate (DSS). These results were compared with homozygous transgenic C57BL/6 mice expressing hReg3α in hepatocytes under the control of the mouse albumin gene promoter. Transgenic hepatocytes secreted hReg3α into blood vessels through the basolateral membranes, and into bile canaliculi through the apical membranes.

Histological score, based on the evaluation of the mucosal architectural change, mononuclear cell infiltration, neutrophil infiltration epithelial defects and Goblet cell loss, was evaluated in colon and distal colon of both groups (results presented in FIG. 10). The severity of the inflammation was stronger in WT mice treated with recombinant hReg3α compared to hReg3α-transgenic mice. These results are particularly significant in the distal colon. Fecal blood score, diarrhea score and body weight loss were also diminished in hReg3α-transgenic mice compared to treated WT mice (FIGS. 11-13) thus leading to better survival rate in transgenic mice (100%) compared to treated WT mice (30%).

Our findings suggest that a modulation of the intraluminal concentration of Reg3α is potent in attenuating intestinal inflammation through a gut microbiota reshaping and with better efficiency than with intravenous administration of Reg3α. Thus administration into the digestive tract of recombinant human Reg3α is a preferred mode of administration as it may lead to better efficacy with a less invasive administration.

Example 3 hReg3α-Transgenic Mice Resist Better to DSS-Induced Colitis after Anti Biotherapy Degradation of the microbiota by antibiotics leads to a potentiation of inflammation and to numerous intestinal and extra-intestinal deleterious effects. We studied the effects of two antibiotics (named Abx), vancomycin and gentamicin, administered during three days on the following response to DSS-induced colitis on WT mice and hReg3α transgenic mice. Vancomycin is a tricyclic glycopeptide that kills most gram-positive organisms by binding to bacteria cell walls and altering cell membrane permeability. It also interferes with bacteria RNA synthesis. Gentamicin is a broad-spectrum aminoglycoside antibiotic that targets aerobic gram-negative bacilli.

In two independent experiments, we observed a diminished body weight loss and diarrhea score in Abx-transgenic (TG Abx) mice compared to Abx-wild-type mice (WT Abx) and even compare to WT mice which did not had antibiotherapy (WT) (see for example FIG. 14). Fecal blood score was also diminished in Abx-transgenic mice compared to WT Abx mice (see FIG. 15). An analysis of the distal colon from Abx-treated transgenic mice upon DSS showed a clear less severe inflammation and mucosal damage that was significantly decreased over that of Abx-treated WT mice (see histological score on FIG. 16). These results suggest that antibiotic perturbation of the Reg3α-shaped microbiota cannot disrupt intestinal homeostasis and the integrity of intestinal defenses, which protect against intestinal inflammation.

Example 4

Intrarectal Administration of hReg3α Decreased Colon Damage and Inflammation in WT Mice with Colitis We evaluated the effects of intrarectal administrations of rcReg3α in WT mice with colitis. An amount of 100 µg of rcReg3α (rcReg3α; n=14), or an equivalent volume of buffer (n=15) was delivered on the day before and on the day of trinitrobenzesulfonic acid (TNBS) administration.

Indeed an alternative type of colitis can be induced using a single intrarectal administration of trinitrobenzesulfonic acid (TNBS) together with ethanol. In contrast with oral administration of DSS, which destroys colon epithelial cells, alters barrier function, and subsequently causes inflammation, TNBS rapidly triggers a severe colonic inflammation through a T-cell immune response against haptenized proteins and luminal antigens.

The body weight loss was the same in the two groups of mice. Histological stainings revealed that mice given intrarectal rcReg3α showed milder colonic barrier defects and inflammation than mice not given intrarectal rcReg3α. A significant decrease of the inflammatory markers Il1b, Tnf, and myeloperoxidase was observed in the colon tissues of mice given intrarectal rcReg3α. These positive effects of a local administration of a recombinant Reg3α protein indicate that an exogenous hReg3α can contribute to the preservation of gut barrier integrity during colitis and underlines the health relevance of this molecule.

Repeated intravenous administration of rcReg3α were ineffective, whereas rectal administrations of rcReg3α helped to preserve gut barrier integrity during induced colitis in control mice.

Thus, hReg3α provides protection against inflammation and oxidative stress for both the intestinal epithelium and the commensal communities that form the gut microbiota.

The invention claimed is:

1. A method for promoting ex vivo growth of oxygen sensitive gram-positive bacteria comprising contacting said bacteria with a Reg3α polypeptide comprising an amino acid sequence selected from the group consisting of SEQ ID NO: 1, SEQ ID NO: 2, SEQ ID NO: 3 and SEQ ID NO: 4.

2. The method according to claim 1, wherein the oxygen sensitive bacteria are members of the Clostridiales order.

3. The method according to claim 1 wherein the polypeptide comprises the amino acid sequence SEQ ID NO: 1, SEQ ID NO: 2, or SEQ ID NO:3.

4. The method according to claim 1 wherein the gram-positive bacteria belong to the Ruminococcaceae and/or to the Lachnospiraceae.

5. The method according to claim 4 wherein the gram-positive bacteria are selected from the group consisting of *Faecalibacterium prausnitzii* and *Roseburia intestinalis*.

* * * * *

SEQUENCE LISTING

```
<160> NUMBER OF SEQ ID NOS: 4

<210> SEQ ID NO 1
<211> LENGTH: 175
<212> TYPE: PRT
<213> ORGANISM: Homo sapiens

<400> SEQUENCE: 1

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175
```

```
<210> SEQ ID NO 2
<211> LENGTH: 150
<212> TYPE: PRT
<213> ORGANISM: Artificial Sequence
<220> FEATURE:
<223> OTHER INFORMATION: recombinant form

<400> SEQUENCE: 2

Met Glu Glu Pro Gln Arg Glu Leu Pro Ser Ala Arg Ile Arg Cys Pro
1               5                   10                  15

Lys Gly Ser Lys Ala Tyr Gly Ser His Cys Tyr Ala Leu Phe Leu Ser
            20                  25                  30

Pro Lys Ser Trp Thr Asp Ala Asp Leu Ala Cys Gln Lys Arg Pro Ser
        35                  40                  45

Gly Asn Leu Val Ser Val Leu Ser Gly Ala Glu Gly Ser Phe Val Ser
    50                  55                  60

Ser Leu Val Lys Ser Ile Gly Asn Ser Tyr Ser Tyr Val Trp Ile Gly
65                  70                  75                  80

Leu His Asp Pro Thr Gln Gly Thr Glu Pro Asn Gly Glu Gly Trp Glu
                85                  90                  95

Trp Ser Ser Ser Asp Val Met Asn Tyr Phe Ala Trp Glu Arg Asn Pro
            100                 105                 110

Ser Thr Ile Ser Ser Pro Gly His Cys Ala Ser Leu Ser Arg Ser Thr
        115                 120                 125

Ala Phe Leu Arg Trp Lys Asp Tyr Asn Cys Asn Val Arg Leu Pro Tyr
    130                 135                 140

Val Cys Lys Phe Thr Asp
145                 150

<210> SEQ ID NO 3
<211> LENGTH: 149
<212> TYPE: PRT
<213> ORGANISM: Homo sapiens

<400> SEQUENCE: 3

Glu Glu Pro Gln Arg Glu Leu Pro Ser Ala Arg Ile Arg Cys Pro Lys
1               5                   10                  15

Gly Ser Lys Ala Tyr Gly Ser His Cys Tyr Ala Leu Phe Leu Ser Pro
            20                  25                  30

Lys Ser Trp Thr Asp Ala Asp Leu Ala Cys Gln Lys Arg Pro Ser Gly
        35                  40                  45

Asn Leu Val Ser Val Leu Ser Gly Ala Glu Gly Ser Phe Val Ser Ser
    50                  55                  60

Leu Val Lys Ser Ile Gly Asn Ser Tyr Ser Tyr Val Trp Ile Gly Leu
65                  70                  75                  80

His Asp Pro Thr Gln Gly Thr Glu Pro Asn Gly Glu Gly Trp Glu Trp
                85                  90                  95

Ser Ser Ser Asp Val Met Asn Tyr Phe Ala Trp Glu Arg Asn Pro Ser
            100                 105                 110

Thr Ile Ser Ser Pro Gly His Cys Ala Ser Leu Ser Arg Ser Thr Ala
        115                 120                 125

Phe Leu Arg Trp Lys Asp Tyr Asn Cys Asn Val Arg Leu Pro Tyr Val
    130                 135                 140

Cys Lys Phe Thr Asp
145

<210> SEQ ID NO 4
```

```
<211> LENGTH: 138
<212> TYPE: PRT
<213> ORGANISM: Homo sapiens

<400> SEQUENCE: 4

Ile Arg Cys Pro Lys Gly Ser Lys Ala Tyr Gly Ser His Cys Tyr Ala
1               5                   10                  15

Leu Phe Leu Ser Pro Lys Ser Trp Thr Asp Ala Asp Leu Ala Cys Gln
                20                  25                  30

Lys Arg Pro Ser Gly Asn Leu Val Ser Val Leu Ser Gly Ala Glu Gly
            35                  40                  45

Ser Phe Val Ser Ser Leu Val Lys Ser Ile Gly Asn Ser Tyr Ser Tyr
        50                  55                  60

Val Trp Ile Gly Leu His Asp Pro Thr Gln Gly Thr Glu Pro Asn Gly
65                  70                  75                  80

Glu Gly Trp Glu Trp Ser Ser Ser Asp Val Met Asn Tyr Phe Ala Trp
                85                  90                  95

Glu Arg Asn Pro Ser Thr Ile Ser Ser Pro Gly His Cys Ala Ser Leu
            100                 105                 110

Ser Arg Ser Thr Ala Phe Leu Arg Trp Lys Asp Tyr Asn Cys Asn Val
        115                 120                 125

Arg Leu Pro Tyr Val Cys Lys Phe Thr Asp
    130                 135
```